(12) United States Patent
Koenig et al.

(10) Patent No.: US 11,890,060 B2
(45) Date of Patent: Feb. 6, 2024

(54) SYSTEM AND METHOD FOR NAVIGATING AND ILLUSTRATING A PROCEDURE

(71) Applicant: Medtronic Navigation, Inc., Louisville, CO (US)

(72) Inventors: Matthew W. Koenig, Denver, CO (US); Marco Capote, Boulder, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 313 days.

(21) Appl. No.: 16/861,356

(22) Filed: Apr. 29, 2020

(65) Prior Publication Data

US 2021/0338336 A1 Nov. 4, 2021

(51) Int. Cl.
| | | |
|---|---|---|
| A61B 34/20 | (2016.01) | |
| A61B 34/10 | (2016.01) | |
| A61B 34/00 | (2016.01) | |
| G06T 7/38 | (2017.01) | |
| G06T 7/13 | (2017.01) | |
| G06T 7/00 | (2017.01) | |
| G06T 7/60 | (2017.01) | |

(52) U.S. Cl.
CPC ............ *A61B 34/20* (2016.02); *A61B 34/10* (2016.02); *A61B 34/25* (2016.02); *G06T 7/0012* (2013.01); *G06T 7/13* (2017.01); *G06T 7/38* (2017.01); *G06T 7/60* (2013.01); *A61B 2034/102* (2016.02); *A61B 2034/107* (2016.02); *A61B 2034/2059* (2016.02); *G06T 2207/30012* (2013.01); *G06T 2207/30052* (2013.01)

(58) Field of Classification Search
None
See application file for complete search history.

(56) References Cited

U.S. PATENT DOCUMENTS

| | | |
|---|---|---|
| 7,156,876 B2 | 1/2007 | Moumene et al. |
| 7,648,529 B2 | 1/2010 | An et al. |
| 7,697,972 B2 | 4/2010 | Verard et al. |
| RE44,305 E | 6/2013 | Foley et al. |
| 8,644,907 B2 | 2/2014 | Hartmann et al. |
| 8,842,893 B2 | 9/2014 | Teichman et al. |
| 9,408,711 B2 | 8/2016 | Burkinshaw et al. |
| 9,452,016 B2 * | 9/2016 | Moisa .................... A61B 5/287 |

(Continued)

FOREIGN PATENT DOCUMENTS

| | | |
|---|---|---|
| EP | 1442715 A2 | 8/2004 |
| WO | 2019246559 A1 | 12/2019 |

OTHER PUBLICATIONS

Ruikar, Darshan D., Ravindra S. Hegadi, and K. C. Santosh. "A systematic review on orthopedic simulators for psycho-motor skill and surgical procedure training." Journal of medical systems 42 (2018): 1-21. (Year: 2018).*

(Continued)

*Primary Examiner* — Michelle M Entezari
(74) *Attorney, Agent, or Firm* — Harness, Dickey & Pierce, P.L.C.

(57) ABSTRACT

Disclosed is a system to assist in a procedure. During the procedure an object may be moved relative to a subject, such as being positioned and/or placed within a subject. The system and related method may be used to assist in displaying and/or determining a pose of the object relative to a subject, such as rigid portions of a subject.

18 Claims, 11 Drawing Sheets

(56) References Cited

U.S. PATENT DOCUMENTS

| | | |
|---|---|---|
| 9,491,415 B2 | 11/2016 | Deitz et al. |
| 10,117,753 B2 | 11/2018 | Suh et al. |
| 10,292,770 B2 | 5/2019 | Ryan et al. |
| 10,369,006 B2 | 8/2019 | Burkinshaw et al. |
| 10,443,974 B2 | 10/2019 | Finsand |
| 2004/0199072 A1 | 10/2004 | Sprouse et al. |
| 2005/0197814 A1 | 9/2005 | Aram et al. |
| 2005/0240126 A1* | 10/2005 | Foley ............... A61B 8/06 601/2 |
| 2006/0200244 A1 | 9/2006 | Assaker |
| 2007/0276501 A1 | 11/2007 | Betz et al. |
| 2008/0161680 A1 | 7/2008 | von Jako et al. |
| 2010/0092054 A1 | 4/2010 | Hensley et al. |
| 2012/0158060 A1 | 6/2012 | Abrahams et al. |
| 2013/0110241 A1 | 5/2013 | Palmatier et al. |
| 2014/0244220 A1 | 8/2014 | McKinnon et al. |
| 2014/0257411 A1 | 9/2014 | Rezach |
| 2016/0045317 A1 | 2/2016 | Lang et al. |
| 2016/0100955 A1 | 4/2016 | Stinchfield et al. |
| 2016/0338782 A1* | 11/2016 | Bowling ............ A61B 90/39 |
| 2016/0343273 A1* | 11/2016 | Stuart ............... B25J 9/1676 |
| 2016/0371838 A1 | 12/2016 | Neetz |
| 2017/0196643 A1* | 7/2017 | Popovic ............ A61B 34/30 |
| 2017/0367766 A1 | 12/2017 | Mahfouz |
| 2017/0367842 A1 | 12/2017 | Predick et al. |
| 2018/0092699 A1 | 4/2018 | Finley |
| 2018/0110628 A1 | 4/2018 | Sharifi-Mehr et al. |
| 2018/0205935 A1* | 7/2018 | Burakou ........... H04N 13/246 |
| 2018/0303552 A1 | 10/2018 | Ryan et al. |
| 2018/0360544 A1 | 12/2018 | Vanheule et al. |
| 2019/0060007 A1* | 2/2019 | Fossez ............... G16H 20/40 |
| 2019/0167352 A1 | 6/2019 | Mahfouz |
| 2019/0167435 A1 | 6/2019 | Cordonnier |
| 2019/0254756 A1* | 8/2019 | Zhang ............... A61B 90/90 |
| 2019/0254838 A1 | 8/2019 | Miller et al. |
| 2019/0328460 A1 | 10/2019 | Ronen et al. |
| 2019/0336220 A1* | 11/2019 | Hladio ............... A61B 34/10 |
| 2020/0030034 A1 | 1/2020 | Kontaxis et al. |
| 2020/0035348 A1* | 1/2020 | Sartor ............... G16H 30/20 |
| 2020/0205898 A1 | 7/2020 | Hampp et al. |
| 2020/0281742 A1* | 9/2020 | Wu .................... A61B 34/74 |
| 2021/0196381 A1* | 7/2021 | Eckert ............... G16H 40/63 |
| 2021/0354286 A1* | 11/2021 | DiMaio ............. A61B 90/98 |
| 2022/0071769 A1* | 3/2022 | Farley ............... A61B 34/30 |
| 2022/0079675 A1* | 3/2022 | Lang ................. G02B 30/52 |

OTHER PUBLICATIONS

Zheng, Yefeng, et al. "Automatic aorta segmentation and valve landmark detection in C-arm CT for transcatheter aortic valve implantation." IEEE transactions on medical imaging 31.12 (2012): 2307-2321. (Year: 2012).*

Tutunea-Fatan, O. Remus, et al. "Application of collision detection to assess implant insertion in elbow replacement surgery." Medical Imaging 2010: Visualization, Image-Guided Procedures, and Modeling. vol. 7625. SPIE, 2010. (Year: 2010).*

Galanis, Christos C., et al. "Computer methods for automating preoperative dental implant planning: Implant positioning and size assignment." Computer methods and programs in biomedicine 86.1 (2007): 30-38. (Year: 2007).*

Cicek, et al.; 3D U-Net: Learning Dense Volumetric Segmentation from Sparse Annotation, International Conference on Medical Image Computing and Computer-Assisted Intervention, Springer, Cham, pp. 424-432 (2016) (https://arxiv.org/pdf/1606.06650.pdf (2016).

International Search Report and Written Opinion regarding International Application No. PCT/US2021/029430, dated Aug. 19, 2021.

International Search Report and Written Opinion regarding International Application No. PCT/US2021/029426, dated Aug. 6, 2021.

U.S. Appl. No. 16/861,448, filed Apr. 29, 2020, Koenig, et al.

International Preliminary Report on Patentability corresponding to PCT/US2021/029426 dated Oct. 27, 2022.

International Preliminary Report on Patentability corresponding to PCT/US2021/029430, dated Nov. 10, 2022.

* cited by examiner

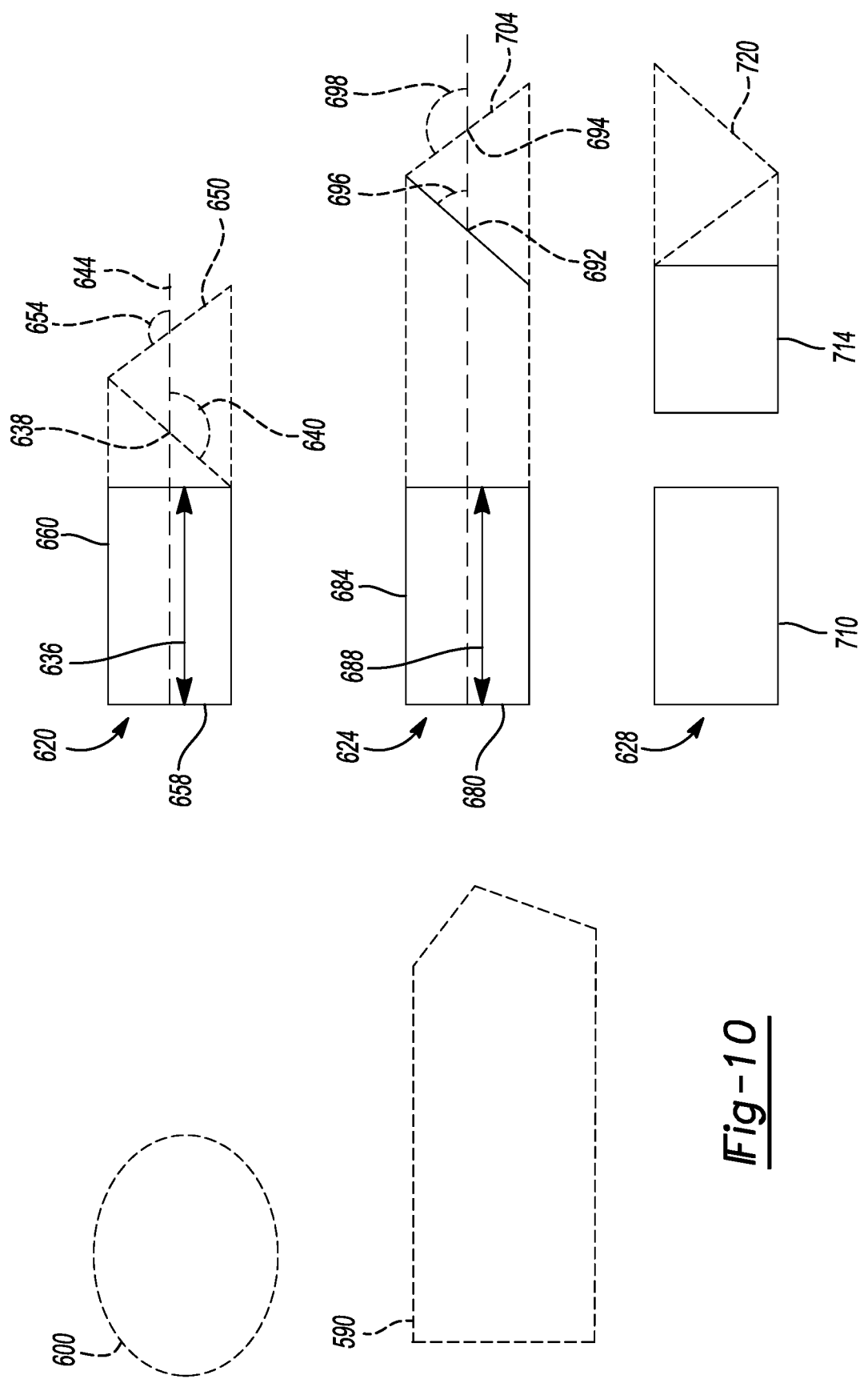

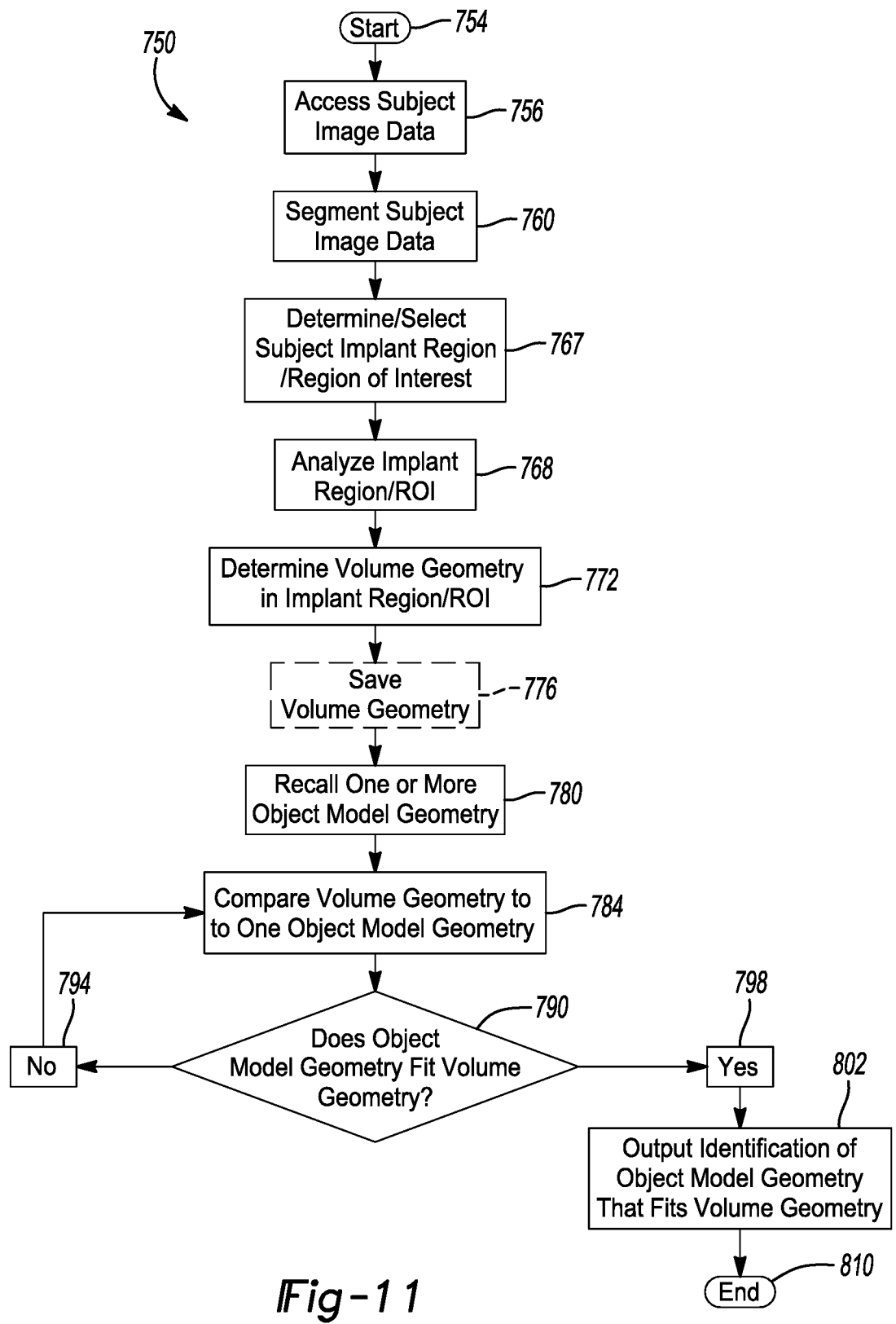

SYSTEM AND METHOD FOR NAVIGATING AND ILLUSTRATING A PROCEDURE

CROSS-REFERENCE TO RELATED APPLICATIONS

This application includes subject matter related to U.S. patent application Ser. No. 16/861,448 filed Apr. 29, 2020. The entire disclosures of each of the above applications are incorporated herein by reference.

FIELD

The subject disclosure relates to a system for performing a procedure, and particularly to a system and method for illustrating an altered and/or current pose of a portion of a subject and/or portion relative to a subject.

BACKGROUND

This section provides background information related to the present disclosure which is not necessarily prior art.

In a navigation system for various procedures, such as surgical procedures, assembling procedures, and the like, an instrument may be tracked. The instrument may be tracked by one or more tracking systems of various operation modes, such as by measuring an effect of an electromagnetic (EM) field on a sensor coil and/or determining a location with optical sensors. The sensor coil may include a conductive material that is placed within an EM field where a current is induced in the sensor coil. The measured induced current may be used to identify or determine a position of the instrument or object.

The electromagnetic field may be generated with a plurality of coils, such as three orthogonally placed coils. Various transmitter or field generation systems include the AxiEM™ electro-magnetic navigation system sold by Medtronic Navigation, Inc., having a place of business in Louisville, Colorado. The AxiEM™ electromagnetic navigation system may include a plurality of coils that are used to generate an electro-magnetic field that is sensed by a tracking device, which may be the sensor coil, to allow a navigation system, such as a StealthStation® surgical navigation system, to be used to track and/or illustrate a tracked position of an instrument.

The tracking system may also, or alternatively, include an optical tracking system. Optical tracking systems include those such as the StealthStation® S7® tracking system. The optical tracking system includes a set of cameras with a field of vision to triangulate a position of the instrument.

SUMMARY

This section provides a general summary of the disclosure, and is not a comprehensive disclosure of its full scope or all of its features.

A system for performing a procedure is disclosed. The procedure may be performed on a living subject such as an animal, human, or other selected patient. The procedure may also or alternatively include any appropriate type of procedure, such as one being performed on an inanimate object (e.g. an enclosed structure, airframe, chassis, etc.). Nevertheless, the procedure may be performed using a navigation system where a tracking system is able to track a selected one or more items.

A navigation system may be used to navigate an object or item, such as an instrument, prosthesis, or implant, relative to a subject for or while performing a procedure. In various embodiments, the procedure may include a procedure on a spine such as a spinal fusion where two or more vertebrae are connected together with a selected implant system or assembly. The implant system may include more than one component that is interconnected at a selected time. Positioning of a portion of the implant system, such as a screw, may be performed relative to a boney structure including a vertebrae. The screw may be positioned into the vertebrae along a selected trajectory and to a selected depth along the trajectory into the vertebrae. In addition to the above example, other appropriate procedures may also be performed relative to and/or on the spine or other appropriate locations.

At a selected time, such as for performing a procedure and/or planning a procedure, image data may be acquired of the subject. Image data may be used to generate an image that is displayed on the display device. The image data may include any appropriate image data such as computed tomography image data, magnetic resonance image data, X-ray cone beam image data (such as with a x-ray cone beam imager). Further, the imager may be any appropriate imager such as the O-arm® imaging system, as discussed further herein. A selected set of instructions, such as a machine learning (e.g. computer vision algorithm), may be used to identify portions within the image data, such as individual vertebrae. The instructions may include a machine learning technique or process, such as a neural network system, that is programed to determine the boundaries (i.e. segment) of selected items, such as one or more vertebrae. The image data may be analyzed substantially or entirely automatically within the neural network to determine the boundaries of the vertebrae.

A selected workflow may be used to efficiently and effectively perform a procedure. The workflow may include analysis or reference to the image data to determine and/or segment selected portions or features in the image, such as segmenting specific vertebrae. The workflow may be used to operate the navigation system in an automatic manner to provide information to a user, such as a clinician or a surgeon, during the performance of the procedure. The image data, having identified boundaries of selected features (e.g. vertebra or vertebra portions), may assist or allow the system in automatically identifying an implant configuration and/or anatomy configuration or pose.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations and are not intended to limit the scope of the present disclosure.

Figures 3A, 3B:
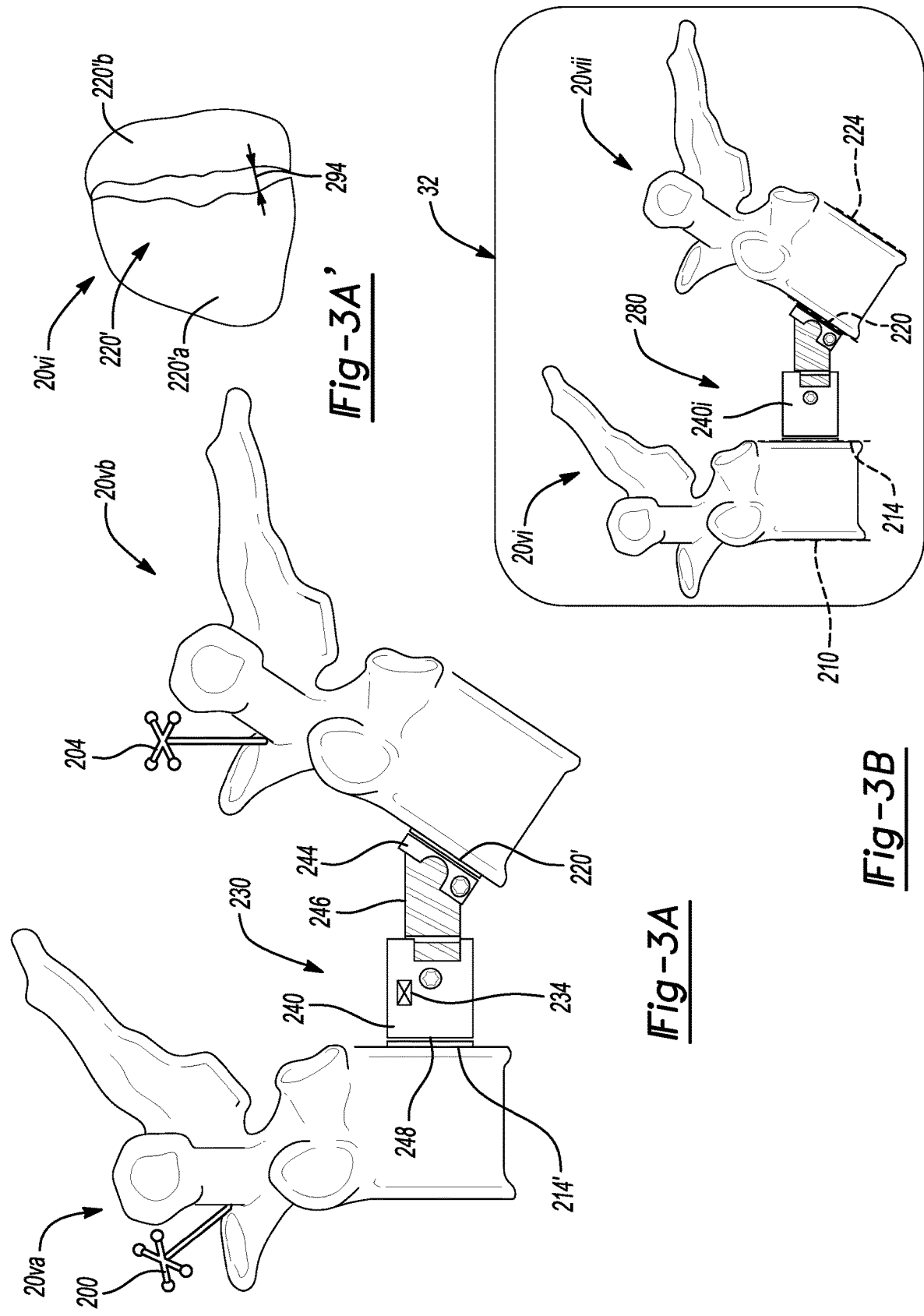
FIG. 3A is a schematic view of a patient space having an exemplary implant position between two vertebrae.
Figure 4A:
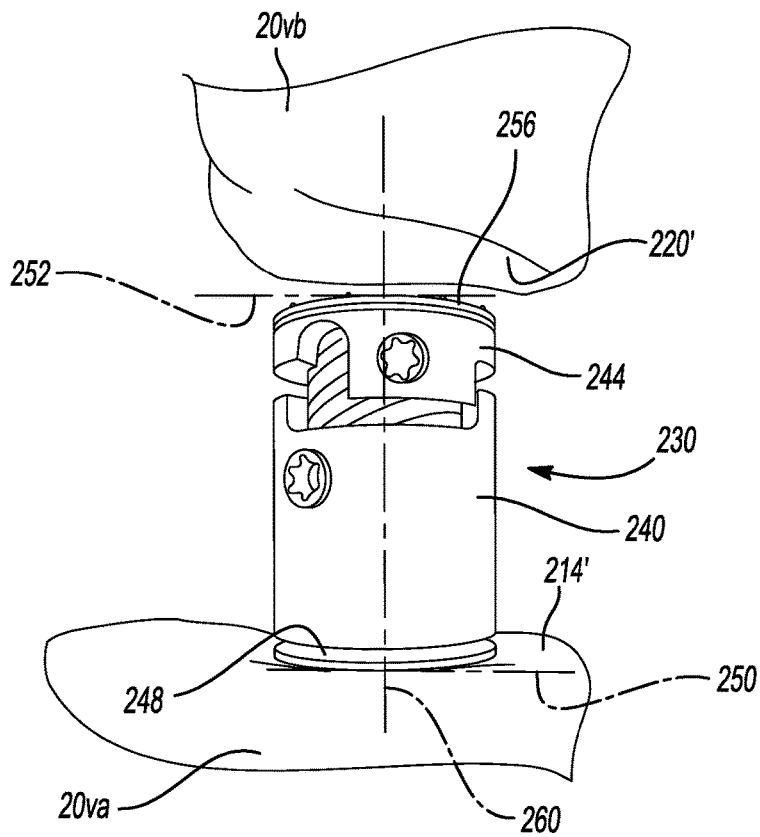
Figure 4B:
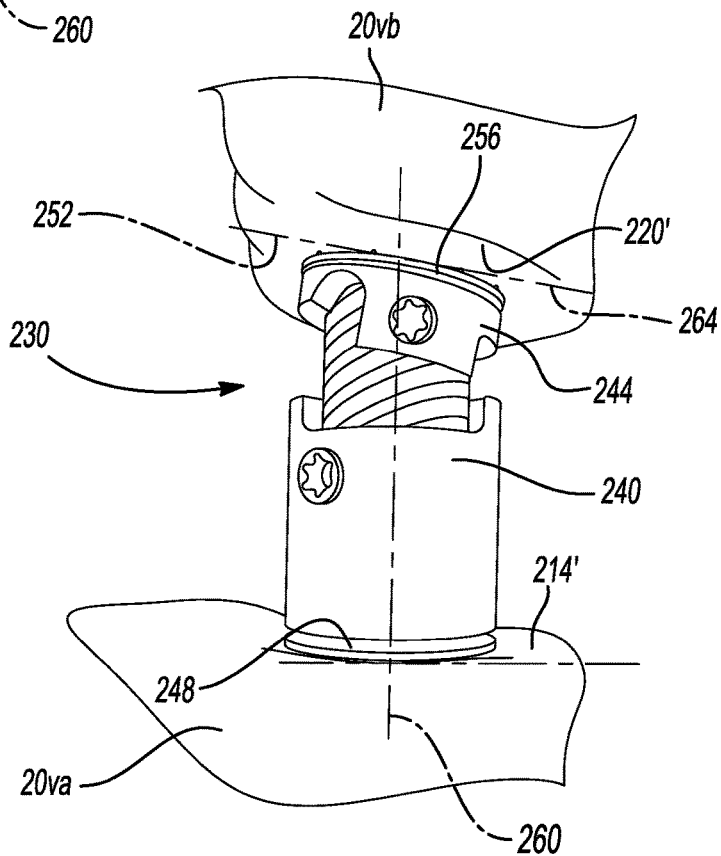
Figure 4C:
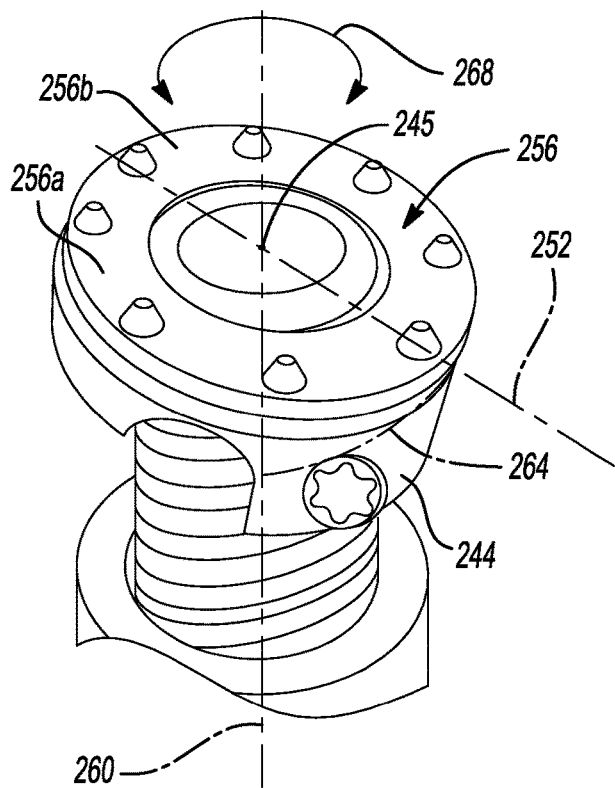
Figure 4D:
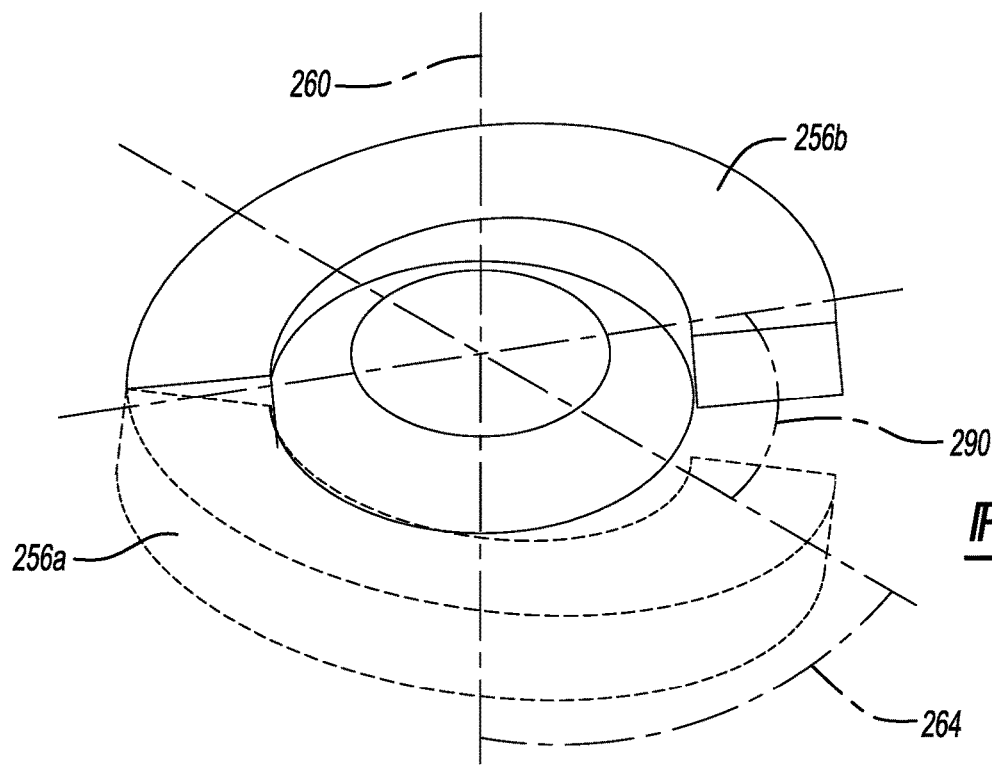
Figure 5:
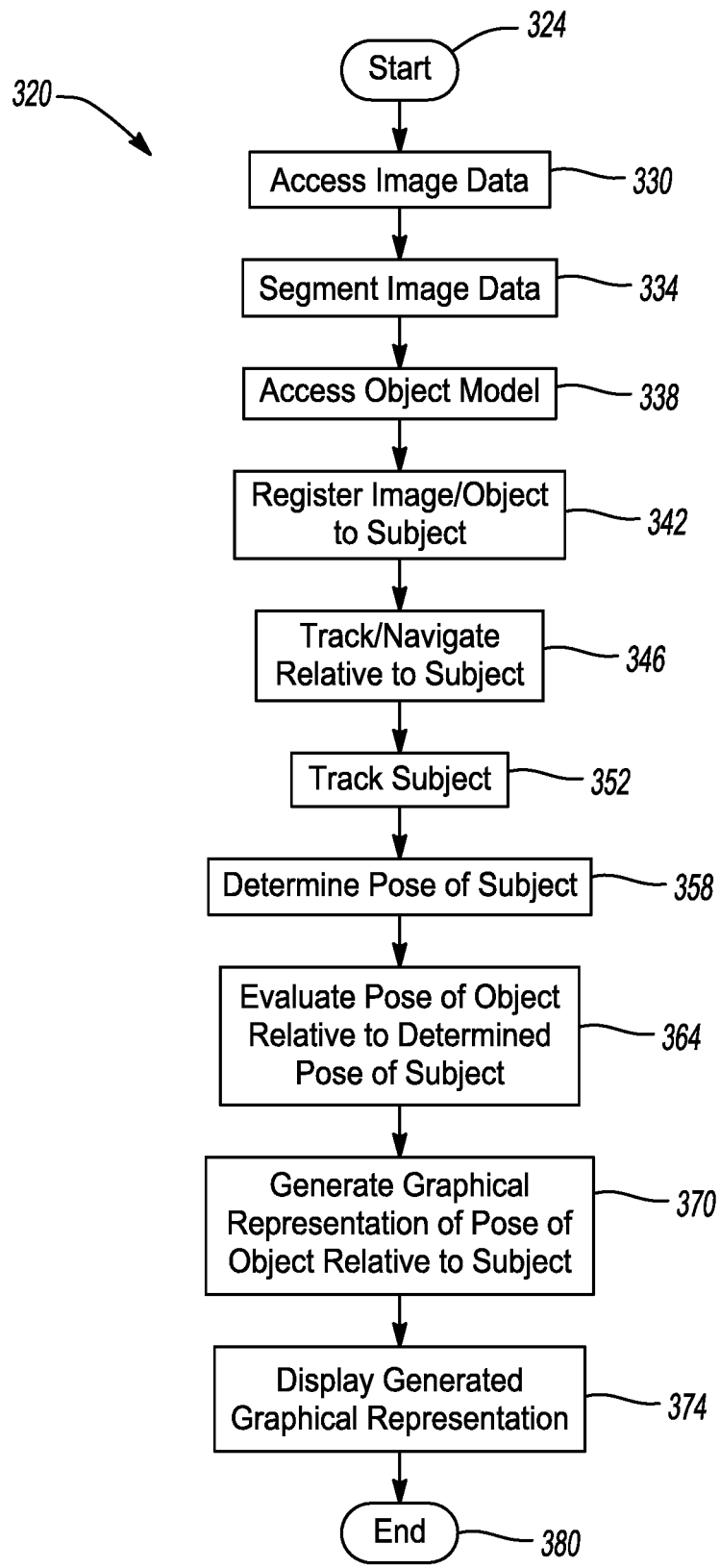
Figure 6:
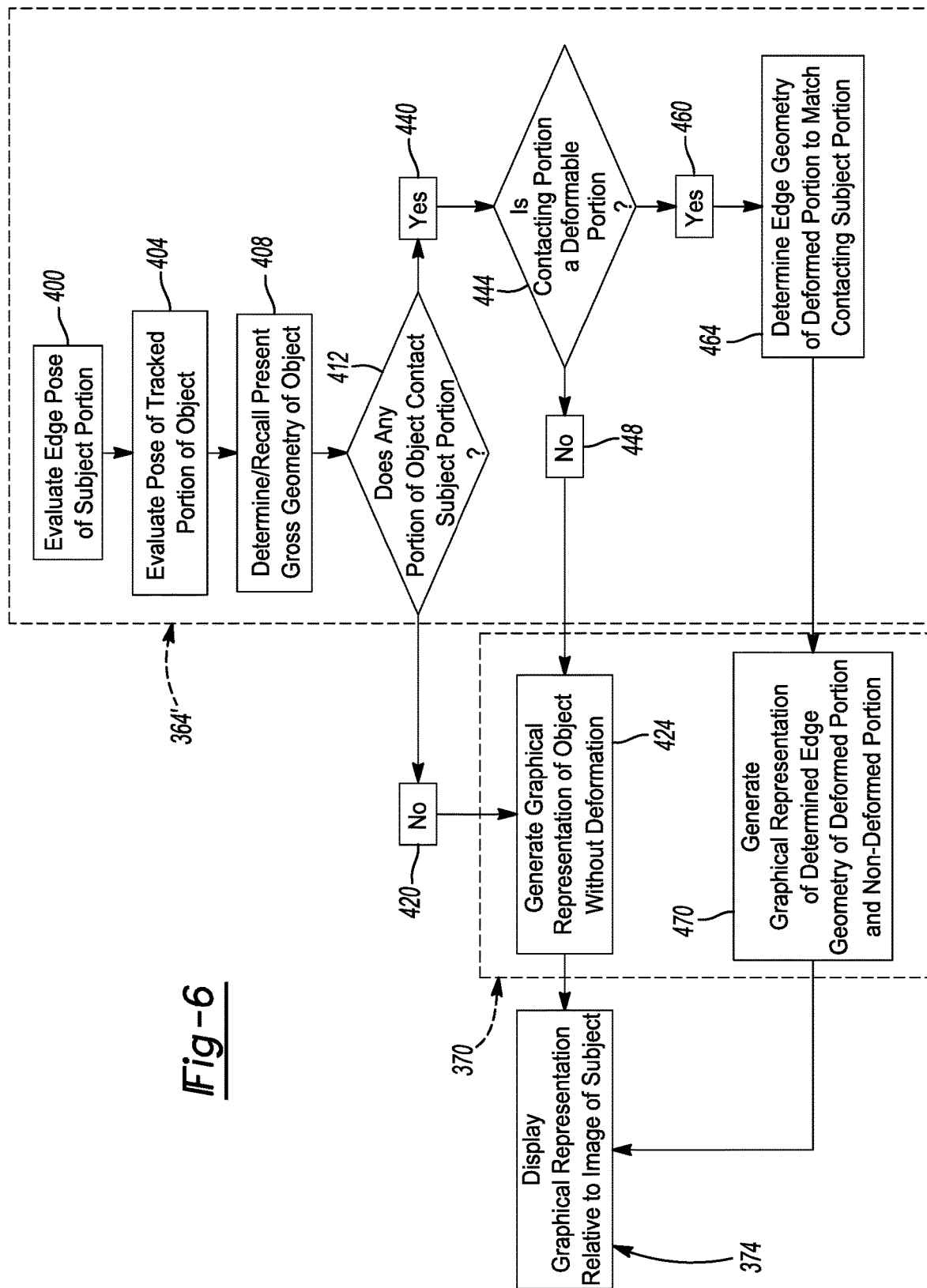
Figure 7:
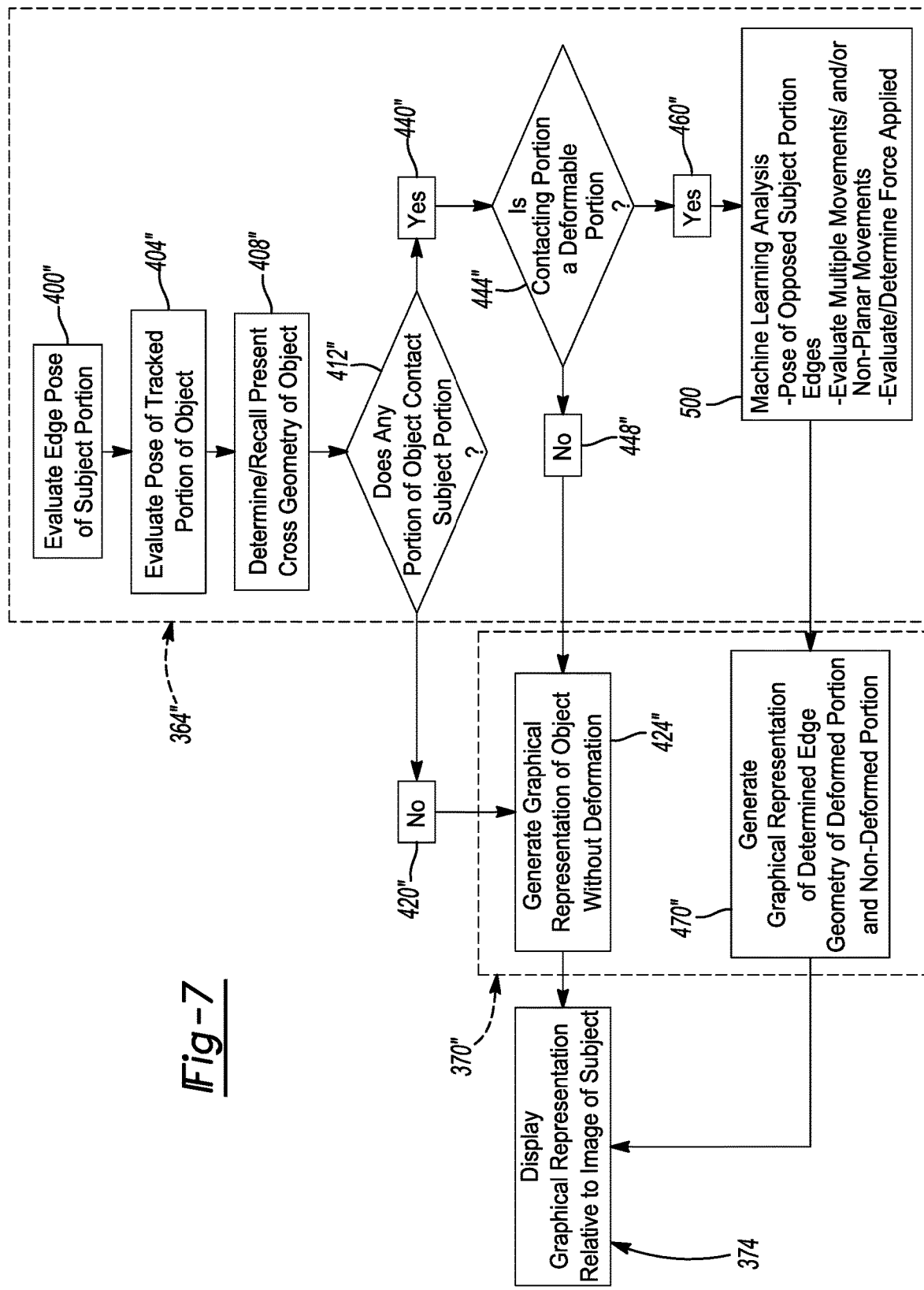
Figure 8:
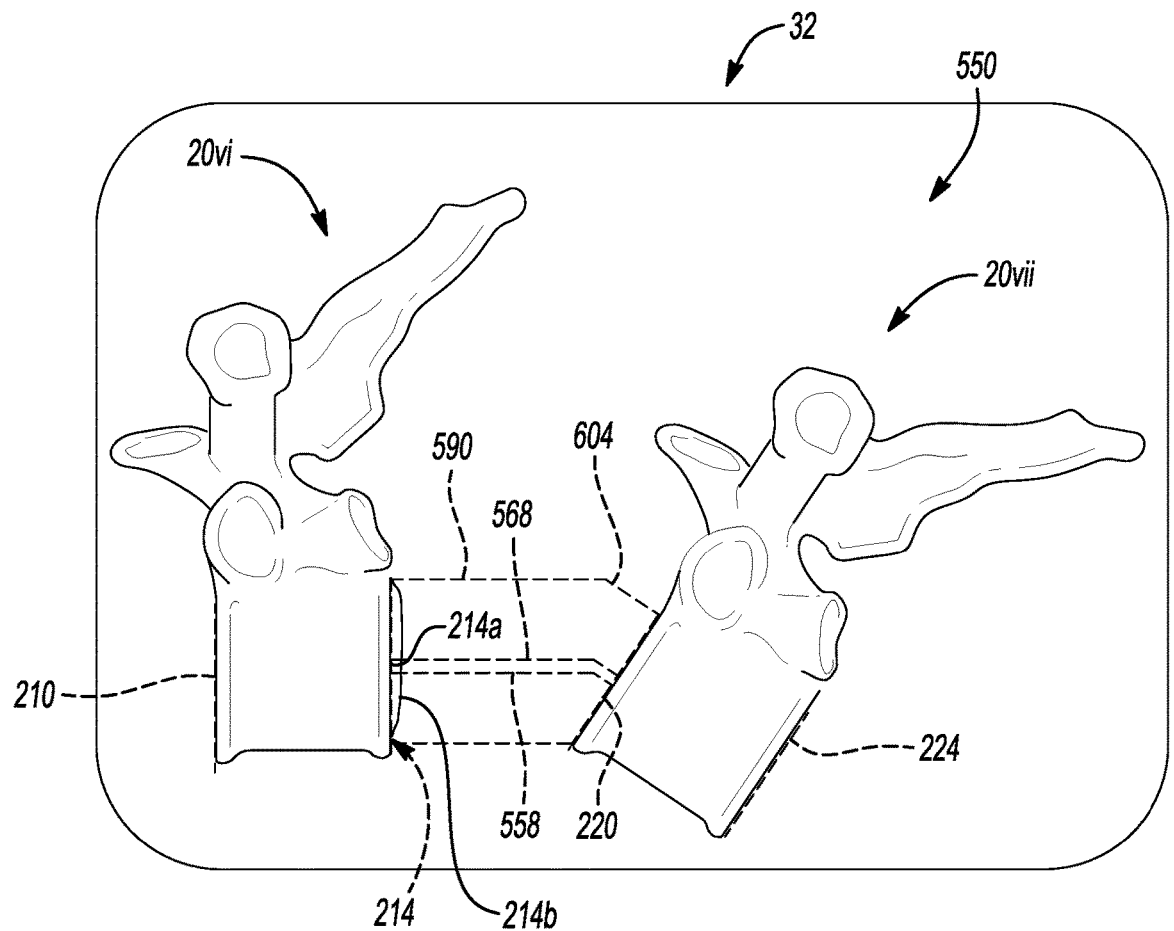
Figure 9:
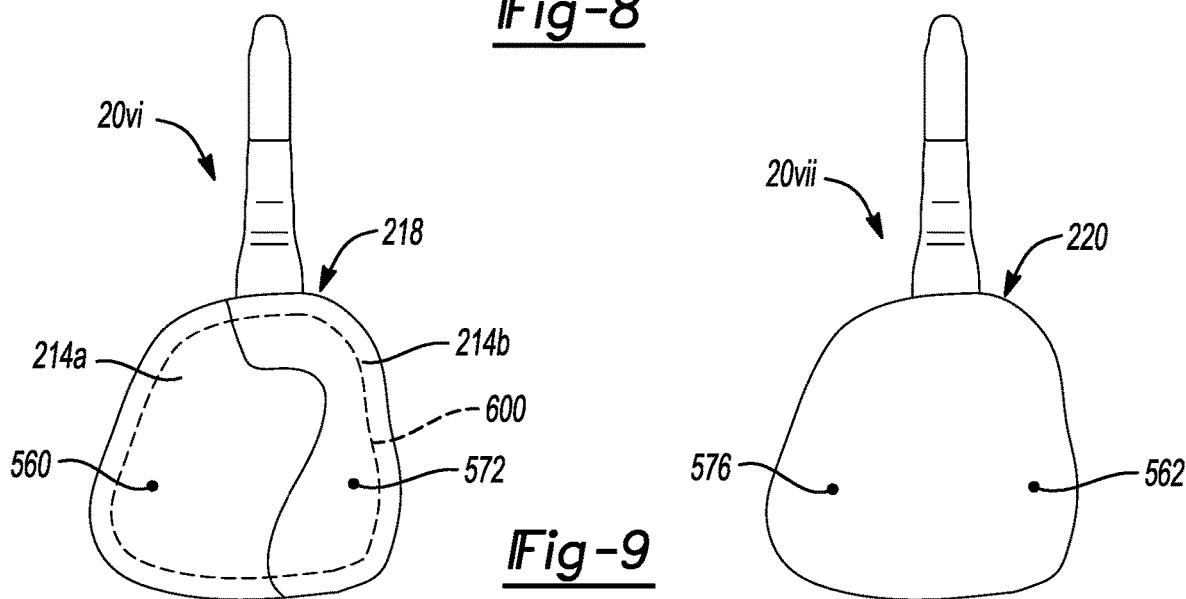

FIG. 3A' is a schematic view of a surface of a vertebrae that is not substantially planar;

FIG. 3B is an exemplary display device user interface of image data and an object;

FIG. 4A is a detailed view of a volume between two vertebrae with an implant device contacting a single surface;

FIG. 4B is a detailed view of a volume between two vertebrae with an implant portion contacting two surfaces;

FIG. 4C is a detailed view of a first end of an implant in a selected configuration;

FIG. 4D is a schematic view of an end of an implant having a variable configuration;

FIG. 5 is a flowchart of a process for determining a proper geometric configuration of an implant and determining and displaying a graphical representation thereof;

FIG. 6 is a detailed subroutine, according to various embodiment, that may be included in FIG. 5;

FIG. 7 is a detailed subroutine, according to various embodiment, that may be included in FIG. 5;

FIG. 8 is a display device view including a user interface for displaying and planning a procedure;

FIG. 9 is a schematic view of end portions of an implant;

FIG. 10 is a view of a multi-configurable implant; and

FIG. 11 is a flowchart of a process for planning a procedure.

Corresponding reference numerals indicate corresponding parts throughout the several views of the drawings.

DETAILED DESCRIPTION

Example embodiments will now be described more fully with reference to the accompanying drawings.

Figure 1:
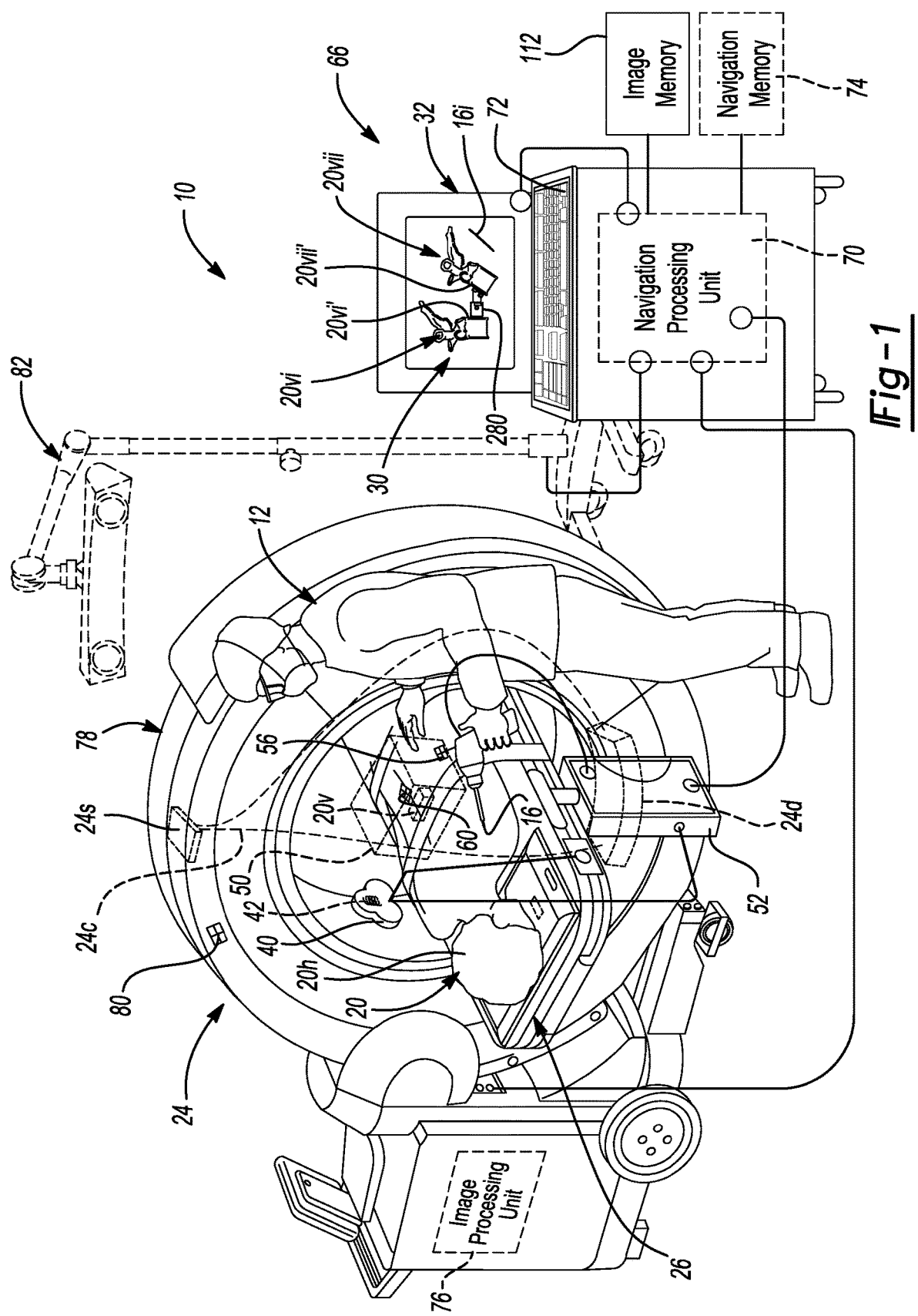
FIG. 1 is an environmental view of a navigation system.

With initial reference to FIG. 1, a navigation system 10 is illustrated. The navigation system 10 may be used for various purposes or procedures by one or more users, such as a user 12. The navigation system 10 may be used to determine or track a pose of an object, such as an instrument 16, in a volume. The pose may include both or all of a three-dimensional location or translational position (X,Y,Z) and orientation (yaw, pitch, and roll). Orientation may include one or more degree of freedom, such as three degrees of freedom. Thus, a pose may include at least six-degree of freedom information. It is understood, however, that any appropriate degree of freedom pose information, such as less than six-degree of freedom pose information, may be determined and/or presented to the user 12.

Tracking the pose of the instrument 16 may assist the user 12 in determining a pose of the instrument 16, even if the instrument 16 is not directly viewable by the user 12. Various procedures may block the view of the user 12, such as performing a repair or assembling an inanimate system, such as a robotic system, assembling portions of an airframe or an automobile, or the like. Various other procedures may include a surgical procedure, such as performing a spinal procedure, neurological procedure, positioning a deep brain simulation probe, or other surgical procedures on a living subject. In various embodiments, for example, the living subject may be a human subject 20 and the procedure may be performed on the human subject 20. It is understood, however, that the instrument 16 may be tracked and/or navigated relative to any subject for any appropriate procedure. Tracking or navigating an instrument for a procedure, such as a surgical procedure, on a human or living subject is merely exemplary.

Nevertheless, in various embodiments, the surgical navigation system 10, as discussed further herein, may incorporate various portions or systems, such as those disclosed in U.S. Pat. Nos. RE44,305; 7,697,972; 8,644,907; and 8,842,893; U.S. Pat. App. Pub. No. 2004/0199072, and U.S. Pat. App. Pub. No. 2019/0328460 all incorporated herein by reference. The navigation systems may be used to track a pose of an object, as discussed herein. The pose may then be displayed for viewing by the user 12, as also discussed herein.

Various components or systems of the navigation system 10 may include an imaging system 24 that is operable to image the subject 20, such as an O-arm® imaging system (sold by Medtronic, Inc. having a place of business in Minnesota), magnetic resonance imaging (MRI) system, computed tomography system, etc. A subject support 26 may be used to support or hold the subject 20 during imaging and/or during a procedure. The same or different supports may be used for different portions of a procedure.

In various embodiments, the imaging system 24 may include a source 24s. The source may emit and/or generate X-rays. The X-rays may form a cone 24c, such as in a cone beam, that impinge on the subject 20. Some of the X-rays pass though and some are attenuated by the subject 20. The imaging system 24 may further include a detector 24d to detect the X-rays that are not completely attenuated, or blocked, by the subject 20. Thus, the image data may include X-ray image data. Further, the image data may be two-dimensional (2D) image data. It is understood, however, that other or different image data may be acquired such as magnetic resonance image data, positron emission tomography, or other appropriate image data. In various embodiments, different image data from different modalities may be combined or registered to each other for use and navigation.

Image data may be acquired, such as with one or more of the imaging systems discussed above, during a surgical procedure or acquired prior to a surgical procedure for displaying an image 30 on a display device 32. In various embodiments, the acquired image data may also be used to form or reconstruct selected types of image data, such as three-dimensional volumes, even if the image data is 2D image data. The instrument 16 may be tracked in a trackable volume or a navigational volume by one or more tracking systems. Tracking systems may include one or more tracking systems that operate in an identical manner or more and/or different manner or mode. For example, the tracking system may include an electro-magnetic (EM) localizer 40, as illustrated in FIG. 1. In various embodiments, it is understood by one skilled in the art, that other appropriate tracking systems may be used including optical, radar, ultrasonic, etc. The discussion herein of the EM localizer 40 and tracking system is merely exemplary of tracking systems operable with the navigation system 10. The pose, including three dimensional location or translational position (X,Y,Z) and orientation (yaw, pitch, and roll), of the instrument 16 may be tracked in the tracking volume relative to the subject 20 and then illustrated as a graphical representation, also referred to as an icon, 16i with the display device 32. In various embodiments, the icon 16i may be superimposed on the image 30 and/or adjacent to the image 30. As discussed herein, the navigation system 10 may incorporate the display device 30 and operate to render the image 30 from selected image data, display the image 30, determine the pose of the instrument 16, determine the pose of the icon 16i, etc.

With reference to FIG. 1, the EM localizer 40 is operable to generate electro-magnetic fields with a transmitting coil array (TCA) 42 which is incorporated into the localizer 40. The TCA 42 may include one or more coil groupings or arrays. In various embodiments, more than one group is included and each of the groupings may include three coils, also referred to as trios or triplets. The coils may be powered to generate or form an electro-magnetic field by driving current through the coils of the coil groupings. As the current is driven through the coils, the electro-magnetic fields generated will extend away from the coils 42 and form a navigation domain or volume 50, such as encompassing all or a portion of a head 20h, one or more spinal vertebrae 20v, or other appropriate portion. The coils may be powered through a TCA controller and/or power supply 52. It is understood, however, that more than one of the EM localizers 40 may be provided and each may be placed at different and selected locations.

The navigation domain or volume 50 generally defines a navigation space or patient space. As is generally understood in the art, the instrument 16, such as a drill, lead, implant, etc., may be tracked in the navigation space that is defined by a navigation domain relative to a patient or subject 20 with an instrument tracking device 56. For example, the instrument 16 may be freely moveable, such as by the user 12, relative to a dynamic reference frame (DRF) or patient reference frame tracker 60 that is fixed relative to the subject 20. Both the tracking devices 56, 60 may include tracking portions that are tracking with appropriate tracking systems, such as sensing coils (e.g. conductive material formed or placed in a coil) that senses and are used to measure an electromagnetic field strength, optical reflectors, ultrasonic emitters, etc. Due to the tracking device 56 connected or associated with the instrument 16, relative to the DRF 60, the navigation system 10 may be used to determine the pose of the instrument 16 relative to the DRF 60.

The navigation volume or patient space may be registered to an image space defined by the image 30 of the subject 20 and the icon 16i representing the instrument 16 may be illustrated at a navigated (e.g. determined) and tracked pose with the display device 32, such as superimposed on the image 30. Registration of the patient space to the image space and determining a pose of a tracking device, such as with the tracking device 56, relative to a DRF, such as the DRF 60, may be performed as generally known in the art, including as disclosed in U.S. Pat. Nos. RE44,305; 7,697, 972; 8,644,907; and 8,842,893; and U.S. Pat. App. Pub. No. 2004/0199072, all incorporated herein by reference.

The navigation system 10 may further include a navigation processing or processor system 66. The navigation processor system 66 may include the display device 32, the TCA 40, the TCA controller 52, and other portions and/or connections thereto. For example, a wire connection may be provided between the TCA controller 52 and a navigation processor module or unit 70. The processor module or unit, as discussed herein, may be any appropriate type of general or specific processor configured or operable to execute instructions or perform selected functions. Further, the navigation processor system 66 may have one or more user control inputs, such as a keyboard 72, and/or have additional inputs such as from communication with one or more memory systems 74, either integrated or via a communication system. The navigation processor system 66 may, according to various embodiments include those disclosed in U.S. Pat. Nos. RE44,305; 7,697,972; 8,644,907; and 8,842, 893; and U.S. Pat. App. Pub. No. 2004/0199072, all incorporated herein by reference, or may also include the commercially available StealthStation® or Fusion™ surgical navigation systems sold by Medtronic Navigation, Inc. having a place of business in Louisville, CO.

Tracking information, including information regarding the electromagnetic fields sensed with the tracking devices 56, 60, may be delivered via a communication system, such as the TCA controller, which also may be a tracking device controller 52, to the navigation processor system 66 including the navigation processor 70. Thus, the tracked pose of the instrument 16 may be illustrated as the icon 16i relative to the image 30. Various other memory and processing systems may also be provided with and/or in communication with the processor system 66, including the memory system 72 that is in communication with the navigation processor 70 and/or an imaging processing unit 76.

The image processing unit 76 may be incorporated into the imaging system 24, such as the O-arm® imaging system, as discussed above. The image processing unit 76 may also include an appropriate processor module and/or memory module and/or be in communication with the navigation processing unit 66. The imaging system 24 may, therefore, include various portions such as the source 24s and the x-ray detector 24d that are moveable within a gantry 78. The imaging system 24 may also be tracked with a tracking device 80. It is understood, however, that the imaging system 24 need not be present while tracking the tracking devices, including the instrument tracking device 56. Also, the imaging system 24 may be any appropriate imaging system including a MRI, CT, etc.

In various embodiments, the tracking system may include an optical localizer 82. The optical localizer 82 may include one or more cameras that view or have a field of view that defines or encompasses the navigation volume 50. The optical localizer 82 may receive light (e.g. infrared or ultraviolet) input to determine a pose or track the tracking device, such as the instrument tracking device 56. It is understood that the optical localizer 82 may be used in conjunction with and/or alternatively to the EM localizer 40 for tracking the instrument 16.

Information from all of the tracking devices may be communicated to the navigation processor 70 for determining a pose of the tracked portions relative to each other and/or for localizing the instrument 16 relative to the image 30. The imaging system 24 may be used to acquire image data to generate or produce the image 30 of the subject 20. It is understood, however, that other appropriate imaging systems may also be used. The TCA controller 52 may be used to operate and power the EM localizer 40, as discussed above.

The image 30 that is displayed with the display device 32 may be based upon image data that is acquired of the subject 20 in various manners. For example, the imaging system 24 may be used to acquire image data that is used to generate the image 30. It is understood, however, that other appropriate imaging systems may be used to generate the image 30 using image data acquired with the selected imaging system. Imaging systems may include magnetic resonance imagers, computed tomography imagers, and other appropriate imaging systems. Further the image data acquired may be two dimensional or three dimensional data and may have a time varying component, such as imaging the patient during a heart rhythm and/or breathing cycle.

In various embodiments, the image data is a 2D image data that is generated with a cone beam. The cone beam that is used to generate the 2D image data may be part of an imaging system, such as the O-arm® imaging system. The 2D image data may then be used to reconstruct a 3D image or model of the imaged subject, such as the patient 20. The reconstructed 3D image and/or an image based on the 2D image data may be displayed. Thus, it is understood by one skilled in the art that the image 30 may be generated using the selected image data.

Further, the icon 16i, determined as a tracked pose of the instrument 16, may be displayed on the display device 32 relative to the image 30. In addition, the image 30 may be segmented, for various purposes, including those discussed further herein. Segmentation of the image 30 may be used determine and/or delineate objects or portions in the image. The delineation may include or be made as a mask that is represented on a display. The representation may be shown on the display such as with a graphical overlay of a mask, which may also be referred to as an icon. The icon may be the segmented mask and may not be simplified in any manner. In various embodiments, the delineation may be used to identify boundaries of various portions within the image 30, such as boundaries of one or more structures of the patient that is imaged, such as the vertebrae 20v. Accordingly, the image 30 may include an image of one or more of the vertebrae 20v, such as a first vertebrae 20vi and a second vertebrae 20vii. As discussed further herein, the vertebrae, such as the first and second vertebrae 20vi, 20vii may be delineated in the image which may include and/or assist in determining boundaries in images, such as 3D and 2D images. In various embodiments, the delineation may be represented such as with an icon 20vi' or a second icon 20vii'. The boundaries 20vi', 20vii' may be determined in an appropriate manner and for various purposes, as also discussed further herein. Further, the icon may be used to represent, for display, a selected item, as discussed herein, including the delineation of the object, boundary, etc.

According to various embodiments, the image 30 may be segmented in a substantially automatic manner. In various embodiments, the automatic segmentation may be incorporated into a neural network, such as a convolutional neural network (CNN). The CNN may be taught or learn to determine, such as with a probability or prediction, various features, according to various embodiments. Various features may include objects (e.g. vertebra) or parts or portions of objects (e.g. pedicle), and segmentations or boundaries of these objects or portions. The selected segmentations may include identifying a segmentation of selected vertebrae, such as the first vertebrae 20vi and the second vertebrae 20vii. The selected segmentation may be displayed with a selected graphical representation such as a segmentation icon or representation 20vi' and 20vii' for display on the display device 32.

The icons are displayed alone on the display 32 and/or superimposed on the image 30 for viewing by a selected user, such as the user 12 which may be a surgeon or other appropriate clinician. Moreover, once identified, the boundaries or other appropriate portion, whether displayed as icons or not, may be used for various purposes. The boundaries may identify a physical dimension of the vertebrae, poses of the vertebrae in space (i.e. due to registration of the image 30 to the subject 20 as discussed above), possible identified trajectories (e.g. for implantation placement), or the like. Therefore, the image 30 may be used in planning and/or performing a procedure whether the icons 20vi', 20vii' are displayed or the geometry of the boundaries is only determined and not displayed as an icon.

Figure 2:
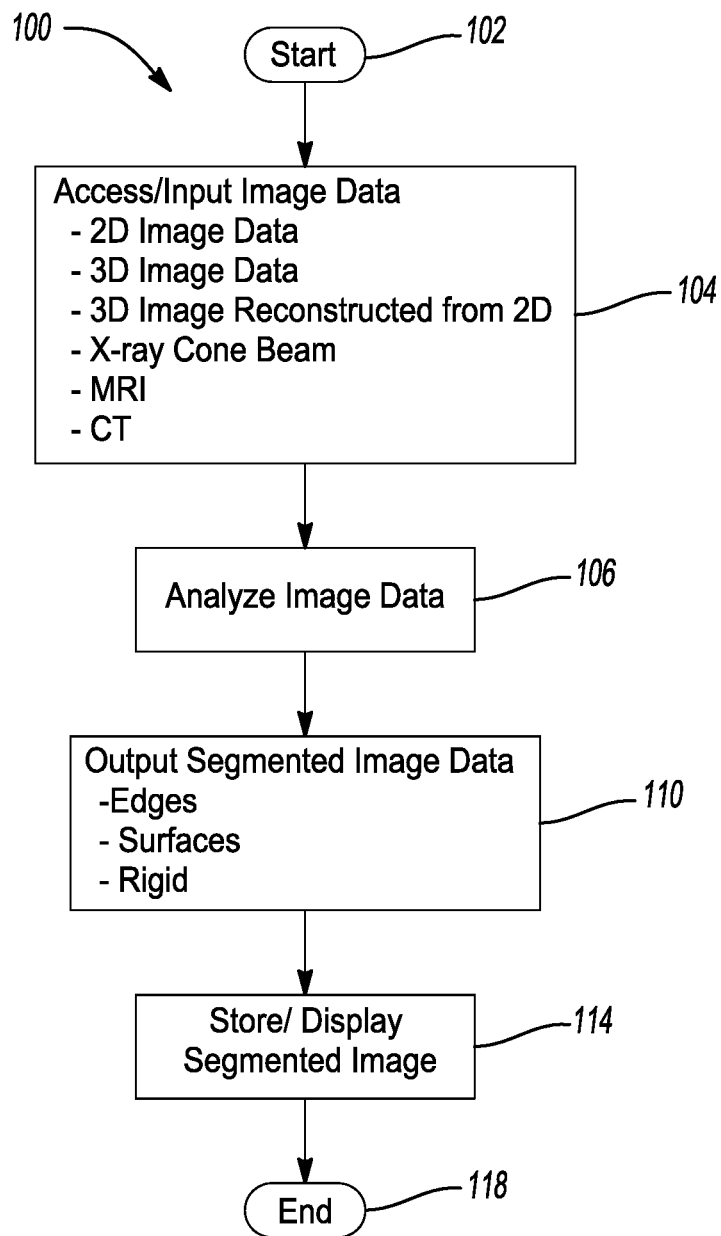
FIG. 2 is a schematic flowchart of a segmentation process.

Turning reference to FIG. 2, a process or method for identifying a portion of an image, also referred to as segmenting an image, is illustrated in the flowchart 100. The flowchart 100, is a general flowchart and a more specific process or any specific process may be used to determine image portions, such as segmentation thereon. Generally, however, the segmentation process begins with an input of image data. The image data may include any appropriate image data such as computed tomography image data, magnetic resonance image data, X-ray cone beam image data. Further, the imager may be any appropriate imager such as the O-arm® imaging system, as discussed herein. The O-arm® imaging system may be configured to acquire image data for 360 degrees around a subject and include 2D image data and/or a 3D reconstruction based on the 2D image data. Further, the O-arm® imaging system may generate images with an x-ray cone beam.

The image data may include 2D image data or a 3D model reconstructed from the 2D image data in block 104. The 2D image data or the reconstructed 3D image data may be from an imaging system such as the imaging system 24. The imaging system 24, as discussed above, may include the O-arm® imaging system. The imaging system 24 may generate a plurality of two dimensional image data that may be used to reconstruct a three dimensional model of the subject 20 including one or more of the vertebrae 20v. The input image data may also be acquired at any appropriate time such as during a diagnostic or planning phase rather than in an operating theatre, as specifically illustrated in FIG. 1. Nevertheless, the image data may be acquired of the subject 20 with the imaging system 24 and may be input or accessed in block 104.

The image data from block 104 may be processed with a selected system or according to selected processes, such as segmentation algorithms (e.g. thresholding, edge detection, region growing, clustering, watershed, machine learning), a neural network or an artificial neural network, in block 106. The analysis technique or process, such as the artificial neural network (ANN) may be a selected appropriate type of artificial neural network such as a convolutional neural network (CNN) (e.g. Özgün Çiçek, Ahmed Abdulkadir, Soeren S. Lienkamp, Thomas Brox, Olaf Ronneberger, "3D U-Net: Learning Dense Volumetric Segmentation from Sparse Annotation", International Conference on Medical Image Computing and Computer-Assisted Intervention, Springer, Cham, pp. 424-432 (2016) (https://arxiv.org/pdf/1606.06650.pdf (2016)) and/or U.S. Pat. App. Pub. No. 2019/0328460, both incorporated herein by reference). The CNN may be taught or learn to analyze the input image data from block 104 to segment selected portions of the image data. For example, as discussed above, the CNN in block 106 may be used to identify boundaries of vertebral bodies in the image data from block 104. As discussed above the boundaries of the vertebral bodies may be displayed on the display device 32 either alone and/or in combination with the image 30.

After the analysis from block 106, therefore, an output may include segmented image data or output segmented data may be made in block 110. The outputted segmented data may be stored in a selected memory system, such as the navigation memory 74 or a segmented image memory 112 (See FIG. 1). The output segmented image data may segment selected portions, such as the vertebrae 20v as discussed above, for various purposes.

Accordingly, the flowchart 100 can start in block 102 and then access or input image data in block 104 to output segmented image data (and/or segmented masks) in block 110 and display or store the segmented image data in block 114. The process may then end in block 118 and/or allow for further processing or workflow, as discussed further herein. It is understood that the selected portions of the flowchart or process 100, however, may include a plurality of additional steps in addition to those discussed above. For example, the CNN may be developed and then taught to allow for an efficient and/or fast segmentation of a selected portion of the image data that is accessed or inputted from block 104. The segmentation may be a specific, such as identifying the vertebrae, or general such as identifying selected boundaries or changing contrast in the image data.

As discussed above, in the flow chart 100, image data of the subject 26 may be acquired with a selected imaging system, such as the imaging system 24, and selected portions thereof may be segmented for display on the display device 32. While the segmentation of the image data may be performed in any appropriate manner, the determined boundaries and edges of the selected portions of the image data (e.g. the vertebrae 20v), may be displayed for a selected procedure.

With continuing reference to FIG. 1 and FIG. 2, and additional reference to FIG. 3A, selected vertebrae such as vertebrae 20va and 20vb may be two vertebrae that are imaged for display on the display device, such as displayed as the vertebrae 20vi and 20vii. It is understood that the two vertebrae 20va and 20vb may be any appropriate vertebrae. The two vertebrae 20va and 20vb may be a part of the subject 26 and exist in the navigation space or volume 50. As illustrated in FIG. 3B, the display device 32 may display the image data of the vertebra as 20vi and 20vii. It is understood, however, the portion illustrated may be one or more cervical, thoracic, lumbar or other appropriate structure of the subject.

With initial reference to FIG. 3A, each of the vertebrae 20v may be tracked with the navigation system by having selected tracking elements, such as vertebrae tracking elements or devices 200, 204. The tracking devices 200, 204 may be tracked in or with the navigation system 10 to determine a pose of the respective vertebra 20va, 20vb. As discussed above, the tracking devices 200, 204 may be rigidly connected to the respective vertebras 20va, 20vb. Therefore, movement of the tracking devices 200, 204 may be used to determine a movement, including a current pose, of the respective vertebrae 20va, 20vb. The tracking devices 200, 204 may be any appropriate tracking devices such as, for example, including EM tracking elements, optical tracking elements, acoustic tracking elements, or combinations thereof. Accordingly, the navigation system 10 may be used to track the pose and/or movement of the respected tracking devices 200, 204 and this may be used to determine a pose of the respective vertebrae 20va, 20vb.

As is generally understood by one skilled in the art, as the tracking device 200, for example, moves if it is rigidly connected to the vertebra 20va, a pose of the vertebra 20va may be determined. For example, the tracking device 200 may be associated with (e.g. rigidly connected or connected to) the vertebra 20va at a selected time. The pose of the tracking device 200 may then be known relative to the vertebrae 20va. Due to registration of the subject 26, including the vertebrae 20va, to the image, movement of the tracking device 200 may be used to determine the movement of all portions of the vertebrae 20va and this may be used to determine a current pose for display on the display device 32 of the respective vertebrae image, such as the vertebrae 20vi.

In addition, as discussed above, the image may be segmented such that various portions, such as boundaries, of the vertebrae may be identified and displayed. For example, as illustrated in FIG. 3B, the vertebrae 20vi may have all of the boundaries identified and/or various portions, such as end plates thereof. For example, the vertebrae 20vi may have a superior end plate 210 identified and delineated on the image with the display device 32. It is understood that various geometry may also be displayed relative to the delineated end plate 210 such as a plane, line, and the like. Similarly the vertebrae 20vi may have a second or posterior end plate 214 identified and delineated. The end plate graphic representations 210, 214 may be displayed on the display device 32 for viewing by the user 12 and/or analysis relative to other portions. In various embodiments a plurality of image portions may be displayed such as also identifying end plates of the second vertebrae. Accordingly, a superior end plate 220 of the second vertebrae 20vii may be delineated and illustrated on the display device as may be an inferior end plate 224 of the vertebrae 20vi.

The identification of various surface or edges of the image portions may be used to analyze and/or illustrate poses and/or movements of various portions. It is further understood, however, that any appropriate edge may be segmented and delineated, such as a femoral head, tibia, etc. For example, as illustrated in FIG. 3B, the end plates may be illustrated on the display device 32 to illustrate a pose of the various end plates relative to one another. The end plates may be displayed either alone or in combination with image portions, such as the images of the vertebrae 20vi, 20vii. Accordingly, display 32 may display only generated graphical representations (e.g. end plate displays) and/or only image portions (e.g. segmented vertebrae 20vi, 20vii), or combinations thereof, as illustrated in FIG. 3B. Nevertheless, as the tracking device, for example the tracking device 200, move the display of the image with the display device 32 may be updated, such as in substantially real time, to illustrate a pose of the various components, such as the vertebrae 20vi. It is understood, therefore, that the plurality of tracking devices, such as the first tracking device and second tracking device 200, 204 may be tracked with the navigation system 10 that is able to update and display the respective poses of the vertebrae with the display device 32.

While the tracking devices 200, 204 may be used to track a current pose of the respective vertebrae 20va, 20vb it is understood that tracking devices may be associated with any appropriate portions, such as other portions of the subject 26 and/or the instrument 16 and/or an implant 230. The implant 230 may be positionable relative to various portions of the subject 26, such as between the vertebrae 20va, 20vb. The vertebrae 20va, 20vb may have substantially ridged portions, such as end plates thereof, that may be segmented in the image (e.g. as discussed above), and also on the vertebrae themselves. For example, the vertebrae 20va may have the inferior end plate 214' of the vertebrae 20va and the vertebrae 20vb may have the superior end plate 220'. The end plates 214', 220' may relate to respective segmented and delineated end plates 214, 220 displayed on the display device 32. Accordingly, because the vertebrae 20va, 20vb are rigid, the end plates move when any portion of the respective vertebrae move. Thus, the poses of the end plates 214', 220' may be determined by tracking the tracking devices 200, 204 that are fixed to the rigid vertebrae 20va, 20vb. Tracking the vertebrae with the tracking devices fixed thereto allow for a substantially real time update of a pose and tracking of movement of the respective end plates 214', 220' for display as delineated end plates 214, 220 with the display device 32.

The implant 230, or other appropriate trackable object, may have a tracking device 234 associated therewith. The tracking device 234 may be used to track a selected portion of the implant 230, such as a first or base portion 240. The implant 230 may also have a second or extension portion 244. The two portions 240, 244 of the implant 230 may move relative to one another, as discussed further herein. Nevertheless, the tracking device 234 may be used to track the implant 230 by association with at least one portion of the implant 230. In various embodiments, the tracking device 234 may be rigidly fixed to a selected one of the portions of the implant 230, such as the main or base portion 240. Thus, the pose of the second portion 240 of the implant 230 may not be directly known by the tracking device 234 or due to the tracking device 234. As discussed above, the navigation system 10 may be used to determine the pose or movement of the tracking device 234 and the pose of various portions relative thereto may be determined due to known geometries or rigid configurations relative to the tracking device 234.

With continuing reference to FIG. 3A and brief reference to FIG. 4A, the implant 234 may be positioned to contact the end plates 214', 220'. As discussed above, the first portion 240 may contact the first end plate 214' and the second portion 244 may contact the second end plate 220'. In a first configuration, such as in a non-extended or minimally extended position, the first portion 240 of the implant 230 may have a base surface 248 that extends along an axis or plane 250 that is substantially parallel with a plane 252 of a second surface or plate 256 of the second portion 244. The implant 230 may extend along a long axis 260 and each of the planes 250, 252 in the first configuration may be substantially perpendicular thereto.

With continuing reference to FIG. 4A and additional reference to FIG. 4B and FIG. 4C, the implant 230 may be moved to a second configuration, such as extended along the long axis 260. The first surface 248 of the first portion 240 may contact the end plate 214' and be substantially fixed thereto. The second portion 244 may extend along the axis 260 and contact the end plate 220' and be substantially fixed relative thereto. In contacting the end plate 220', however, the end plate or surface 256 may move to a position that is not perpendicular to the long axis 260 and forms an acute internal angle 264 relative to the plane 252. Thus, the second portion 244 may move relative to the first portion 240 by tilting or moving the surface 256 relative to the long axis 260.

With continuing reference to FIGS. 4A-4C, the second portion 244 may move relative to the axis 260 in a selected manner, such as rotating at an angle relative to the central axis 260, such as generally in the direction of the double headed arrow 268. Thus, the angle 264 may be formed relative to the long axis 260 at substantially any point around the central axis 260. In various embodiments, the position of the second portion 244 relative to the central axis 260 and, therefore, the first portion 240, may be due to the rigid position of the vertebrae 20va, 20vb. Accordingly, the orientation of the first portion 240 relative to the second portion 244 and their relative positions to the central axis 260, that generally extends through the first portion 240, may be based upon the position of the portions of the subject relative to which the implant 230 is positioned.

Further, the implant 230 may have a prior known or a prior model, such as a computer aided design (CAD) model that includes the dimensions and geometry of the implant 230 and/or the possible configurations of the implant 230. The CAD model of the implant 230 may be stored for recall in a selected memory, such as in the navigation memory 74 and/or the image memory 112. The model of the implant 230 may, therefore, be recalled for assisting and illustrating on the display 32 a model or graphical representation of the implant as an implant graphical representation 280.

As noted above, the implant 230 may have the first part 240 and the second part 244, where the second part 244 may move relative to the first part 240. Thus, the second part 244 may be positioned at the angle 264 relative to the central axis 260. In addition, the first or second part, including the respective ends 248, 256 may be formed as multiple pieces that may also move or deform relative to the central axis 260. For example, as illustrated in FIG. 4C and FIG. 4D, the surface or plane 252 may be separated at the end 256 between a first part 256a and a second part 256b. Each of the two parts 256a, 256b may move relative to one another, such as the first part 256a achieving the angle 264 relative to the central axis 260 while the second part 256b may have an obtuse angle 290 relative to the central axis 260, as illustrated in FIG. 4D. Accordingly, it is understood that the implant 230 may have multiple portions that move relative to the selected plane or axis, such as the two portions 256a, 256b, that move relative to the central axis 260. In various embodiment, the second portion 244, including the portion 256, may deform to fit to a surface in a selected manner. The deformation may include plastic or elastic deformation. Accordingly, the implant 230 may include one or more portions that are able to deform through a range of motion and or have a deformable surface to deform to engage a surface, such as a surface of the bone.

The CAD model, which may be accessed and/or recalled by the image processing unit 76 and/or the navigation processing unit 70 may include information regarding all of the portions of the implant 230 that may move relative to one another and/or the ranges of movement of each of the portions of the implant 230. Thus, the CAD model may be used to determine all possible positons or configurations of the implant 230. The model, therefore, may also be used to illustrate a current configuration of the implant, as discussed herein.

In various embodiments, therefore, the display device 32 may be operated to display the implant 230 as the graphical representation 280 relative to the other portions displayed, such as the vertebrae 20vi, 20vii. The implant graphical representation 280 may be displayed relative to selected portions, such as rigid portions, including the end plates 214, 220. As discussed above, the end plates 214, 220 may be segmented in the image data and may be segmented to include substantially planar structures, faceted structures, or selected contours. For example, with reference to the vertebrae 20vb, the end plate or surface 220' may include two portions, such as a first lateral portion 220'a and a second portion 220'b. The respective portions 220'a, 220'b may have different geometries and/or dimensions relative to one another. For example, the first portion 220'a may have the surface or portion that is displaced by a distance 294 relative to the second portion 220'b. In this instance, when the implant 230 includes the two parts or portions 256a, 256b, the two portions may move relative to the central axis 260 in a non-uniform manner, as illustrated in FIG. 4D. Again, the geometry of the implant and possible movements thereof may be stored in a selected memory, such as in a CAD model included in the navigation memory 74, and the image may be segmented to identify the different geometries of two portions of the vertebrae 20vb.

As discussed above, the implant 230 may include the tracking device 234 to allow for tracking and navigation of the implant 230, including the first portion 240. Due to the known position of the first portion 240 and a selected position of various portions of the implant (e.g. an amount of extension of the second portions 244 relative to the first portion 240) the geometry of the second portion 244 may be determined, as discussed further herein, relative to the image portions displayed and for display on the display device 32. Generally, with reference to FIG. 5, a geometry of the implant 230 may be displayed in the graphical representation 280.

With initial reference to FIG. 5, therefore, a process or method for determining and illustrating the geometry of the implant 230 on the display device 32 as the graphical representation 280 may include the process 320. The process 320 may occur or be carried out by a processor system, such as the navigation processing unit 70 or the image processing unit 76, executing selected instructions or in any appropriate manner. As understood by one skilled in the art, the process 320 may be incorporated into selected instructions of specific processor design, as discussed herein. The process 320 may begin in start block 324. After starting the process in block 324, which may be initiated by the user 12, the display of the graphical representation 280 may occur according to the process 320. In various embodiments, for example, the process may include accessing image data in block 330 of the subject 20. As discussed above the image data of the subject 20 may include selected portions of the subject, and/or the entire subject, but may include the vertebrae 20va, 20vb. After accessing the image data in block 330 the image data may be segmented in block 334. Segmentation of the image data may occur according to any appropriate process. Segmentation of the image data may include determining gradient edges, surfaces, or the like in the accessed image data from block 330. In various embodiments, for example, segmentation of the image data may be performed with a convolutional neural network (CNN) to identify various surfaces and/or edges in the image data. It is understood that any appropriate segmentation algorithm and/or machine learning system may be used to identify portions in the image data. For example, in various embodiments, the user 12 may select or identify a point or pixel (e.g. with an input to select a pixel on the display device) as a seed pixel for segmentation. The segmentation, such as with the CNN, may be carried out by a processor system, such as the navigation processing unit 70 or the image processing unit 76.

The segmented image data may be used in the process 320 to assist in displaying the graphical representation of the implant 230 for understanding its pose by the user 12 or other appropriate individuals. Accessing an object model in block 338 may occur. The model may be accessed, e.g. recalled form a memory system and/or generated such as by having tracked an instrument that touched one or more points on the implant 230 and determining or inputting possible geometry configurations (e.g. extension or angle limits). The model accessed in block 338 may include an entire geometry of the implant 230, or any appropriate object, including its geometry, material deformation ability (e.g. plastic deformation or flexing), dynamic geometry (e.g. rigid surface movement), and the like. As discussed above the implant 230 may include one or more surfaces that may move relative to other surfaces and/or selected geometry, such as a central axis 260. It is further understood that various implants or objects may include substantially infinitely deformation surfaces (e.g. a deformable fabric or elastic polymer) that may substantially mate with any surface more rigid than the implant. In various embodiments, therefore, the accessed model in block 338 may include definitions of the implant 230 that include deformation of any or all surfaces or selected surfaces upon contact with rigid or segmented surfaces in the image data.

The process 320 may also include registering the object to the subject in block 342. Registering the object to the subject may include registering image data to the subject and tracking the object relative to the subject 20. For example, the accessed image data from block 330 may be registered to the subject 20, as discussed above. Additionally, tracking the object, such as the implant 230, relative to the subject 20 may include tracking or knowing the position of the object 230 and/or portions of the object relative to the tracking device 230. Accordingly, the object may be tracked or navigated relative to the subject in block 348. The subject may also be tracked in block 352. Thus, the relative pose of the subject 20 to the object 230 may be known by tracking the object in block 348 and tracking the subject in block 352. After and/or including registration of the image data in block 342, may allow for displaying a graphical representation, such as the graphical representation 280, relative to the image data on the display device 32 as illustrated above and as discussed further herein.

Upon tracking the subject in block 352, a pose of the subject 20 may be determined in block 358. Determining a pose of the subject in block 358 may include determining a pose of a plurality of portions of the subject 20, such as the vertebra 20va and 20vb relative to one another. The pose of the subject 20 determined in block 258, therefore, may include determining a pose of a plurality of portions, which may be individually tracked portions relative to one another in the subject 20. This allows the pose of one or more portions of the subject 20 to be determined in block 358.

The pose of the subject determined in block 358 may be used to evaluate the pose of the object relative to the determined pose of the subject in block 364. In evaluating the pose of the object, a determination may be made of a pose of various portions of the object, such as the implant 230, relative to various portions of the subject 20. In various embodiments, evaluation of the pose of the object may include a determination of an angle of a single surface of the object 230 relative to another portion thereof, such as the second portion 244 relative to the first portion 240 in light of the determined pose of the subject 258. In certain instances, however, in addition to or alternative to that discussed above, the evaluated pose of the object relative to the determined pose of the subject may include a determination based upon a machine learning system or an appropriate algorithm to determine a position of a plurality of portions of the object 230 relative to determined poses of a plurality of portions of the subject 20. Accordingly, the determination of the pose of the object or evaluation of the pose of the object in block 364 may include a plurality of evaluation methods or processes, as discussed further herein. Determination of the pose of the object and its configuration is discussed further herein.

Based upon evaluated pose in block 364, a generated graphical representation of the object relative to the subject may be made in block 370. A generation of a graphical representation may include a display of a geometric configuration, a display of a detailed outline of the object, a display of the CAD model to represent the object based upon the evaluated relative poses, or other appropriate representations. In various embodiments, as illustrated in FIG. 3B, the object 230 may be displayed as the graphical object 280 that substantially represents the object 230 for viewing and understanding by the user 12. Accordingly, the graphical representation 280 may substantially mimic or represent the object 230 on the display device 32 in real time as it appears in physical or patient space.

The generated graphical representation may then be displayed in block 374. The graphical representation may be displayed, as illustrated in FIG. 3B, as the graphical representation 280 relative to the image portions of the subject 20vi, 20vii. Thus, the object may be displayed for viewing by the user 12, or any appropriate individual. It is further understood that the graphical representation need not be displayed but may simply be determined and evaluated for various purposes, such as later planning, saving for follow up evaluation, or other appropriate purposes.

After generating the graphical representation in block 370 and/or displaying the generated graphical representation in block 374, the process 320 may end in block 380. In ending the process 320 in block 380, the user 12 may complete a procedure on the subject 20, complete a selected portion of the procedure on the subject 20, or other appropriate processes. For example, a procedure may be performed on the subject where a display of the graphical representation is selected. Thus, the user 12 may initiate the process 320 and the process may end in block 380 after the object has been positioned in a selected position, such as in a trial position, implant position, or the like. The display of the generated graphic representation may be used by the user 12 for various purposes later in a procedure and/or in a follow up of a procedure. The process ending at block 380 may simply be for ending after determining of a selected or determined single pose of the object relative to the subject, as discussed above.

With continuing reference to FIG. 5 and additional reference to FIG. 6, as discussed above, the evaluation of the pose of the subject relative to the object may be determined in block 364. It is understood that the evaluation in block 364 may be performed in a plurality of different and/or unique processes that may be performed separately and/or in combination, as discussed further herein. Accordingly, the evaluation in block 364 may be understood to be a general evaluation, according to various embodiments, and may include various sub-routines or sub-steps. Accordingly, with reference to FIG. 6, an exemplary evaluation process 364' is illustrated. The sub-routine 364' may be substituted into block 364 in the process 300, discussed above. It is understood, however, that additional steps and/or sub-routines may also be performed in place of and/or in addition to the sub-routine 364'.

The sub-routine 364' may include evaluating an edge pose of the subject portion in block 400. As discussed above, various subject portions may include vertebrae 20v of the subject. These may be segmented and delineated in the image data, as also discussed above, and an evaluation of a particular edge pose of selected portions of the subject may be made in block 400. For example, a procedure may include placing the implant 230 between the two vertebrae 20vi and 20vii. Thus evaluating an edge pose of both of the vertebrae, particularly the edges that face or oppose each other, may occur in block 400. Evaluation of the edge pose may include determining a geometry of the edges relative to one another. Evaluating a pose of the tracked portion of the object in block 404 may also occur. As discussed above the object 230 may include a tracked portion and a portion movable relative to the tracked portion. Accordingly, the navigation system 10 may track and determine the pose of the tracked portion, such as the first portion 240, of the implant 230.

A determination and/or recall of a present gross geometry of the object in block 408 may occur. A gross geometry of the object may include the pose of the first portion 240, such as relative to the edge 214' and a distance that the second portion 244 has been extended or moved relative to the first portion 240. As discussed above, the implant 230 may include an adjustment mechanism 246 that allows movement of the two portions 240, 244 relative to one another. Thus, the gross geometry may include a length or distance between the first end 248 of the first portion 240 and an end or pivot point 245 (FIG. 4C). The gross geometry may be used to determine if any portion of the object contacts the subject portion in block 412. For example, as illustrated in FIG. 3A, the second portion 244 may contact the vertebrae 20vb. The second portion 244 may contact the end plate 220' of the vertebrae 20vb when the second portion 244 has been extend or moved a selected distance or certain distance from the first portion 240. Accordingly, the determination or recall of the present gross geometry of the object in block 408 may be used to determine if any portion of the object contacts the subject in block 412. The recall or determination may be input (e.g. by the user 12) and/or determined based on an input from the object (e.g. an encoder that transmits an amount of movement).

The determination of whether the object contacts a portion of the subject in block 412 may be based upon tracking the vertebrae 20va, 20vb and/or the implant 230. As discussed above, the navigation system 10 may track the various portions and determine their pose relative to one another based upon the various tracking devices 200, 204, 234. While the navigation system 10 is able to track the first portion 240 due to the pose of the tracking device 234 therewith, the specific geometry of the second portion 244 may be generally independent of the position of the first portion 240 unless it is contacting other portions, such as the vertebrae 20vb. Accordingly, by tracking the implant 230 relative to the two vertebrae 20va, 20vb, the navigation system 10 may assist in determining whether the first and second portions 240, 244 contact portions of the subject 20, such as the vertebrae 20v.

If a determination is made that the object is not contacting the subject in block 412, a NO path 420 may be followed and a generation of a graphical representation may be made, as discussed above, in block 370. The generation of a graphical representation may include the generation of a graphical representation of the object without deformation in block 424. As discussed above, the implant 230 may have a non-deformed or substantially straight or aligned geometry, as illustrated in FIG. 4A when only one portion or no portions are contacting the subject 20. Accordingly, the graphical representation for display on the display device 32 may substantially match the illustration or representation of the implant 230, as illustrated in FIG. 4A. Thus, the graphical representation may be displayed in block 374.

If a determination is made that the object is contacting a subject portion in block 412, a YES path 440 may be followed to determine if the contact causes a deformation of the implant in block 444. Again, the implant 230 may contact the vertebrae 20va, but the first portion 240 may not generally deform or change position relative to the long or central axis 260. Accordingly, the face or end 248 may generally be perpendicular to the long axis 260, as illustrated in FIG. 4A. Thus, a determination that the first portion 240 contacts the vertebrae 20va may lead to a determination that the contact does not cause a deformation in block 444 and, therefore, a NO path 448 may be followed. It is understood that other determinations may be made that no deformation has occurred and the NO path 448 may be followed. If the NO path 448 is followed, a generation of a graphic with no deformation may be made in block 424 and the graphical representation may be displayed in block 374.

If a determination that deformation is occurring, a YES path 460 may be followed. As discussed above and illustrated in FIGS. 3A, 3B, and 4B, the second portion 244 when contacting the vertebrae 20vb may deform or move relative to the long axis 260. As illustrated in FIG. 4B, for example, the end or surface 256 may move at an angle or to an angle 264 relative to the central axis 260. Accordingly, when the determination is that the end point or contact surface 256 is moved a distance enough from the surface 248 that the second portion 244 is able to change angle or move relative to the central axis 260, a determination that a deformation has occurred may be made in block 444 and the YES path 460 may be followed.

A determination of edge geometry of the deformed portion to match a contacting subject portion may be made in block 464. For example, the navigation system, such as the navigation processing unit or processor 70, may evaluate the geometry of the edge of the vertebrae 20v*i* in the image, as discussed above. Given the known or determined geometry of the portion 20v*i* and given that the second portion 244 is contacting the surface 220, a determination may be made that the edge or surface 256 of the second portion 244 is at the same or parallel angle or plane as the edge 220. Thus, the surface 256 may be determined to have a geometry that is parallel to the edge or surface 220 of the vertebrae 20v*i*.

The determination of the edge geometry may include various techniques to determine a selected, e.g. optimal fit that may include one or more fits that achieve a selected outcome. Optimal fits may, therefore, be selected to achieve a range of motion, a size, an availability, a configuration for use, etc. Thus, the optimal fit may also be or include a fit relative to the determined edge portion of the subject portion. The optimal fit may be a fit to a selected threshold (e.g. greater than 50% contact) or other appropriate threshold. Various techniques may include a least square fit technique.

After determining the geometry in block 464, generation of a graphic representation may be made in block 370, as discussed above. The graphical generation may include or be a sub-portion to generate graphical representation of the determined edge or geometry of the deformable portion and non-deformable portion in block 470. To generate the graphical representation of the deformable portion in block 470, the navigation system 10 may generate a graphic, as illustrated in FIG. 3B. The graphical representation may include the first portion 240*i* and the second portion 244*i* having the respective edges in contact with the surfaces 214, 220 in the image for display on the display device 32. After generating the graphical representation in block 470, the graphical representation may be displayed in block 374.

Accordingly, the sub-routine 364' may be used to generate a graphical representation of the implant 230 based upon the determined geometry of the image portions of the subject 20v*i*, 2v*ii*. Thus, the representation 280 on the display device 32 may more accurately match the real geometry or real time geometry of the implant 230, as illustrated in FIG. 3A.

With continuing reference to FIG. 5, and additional reference to FIG. 7, the evaluation of the pose of the object to the subject may occur according to sub-routine 364", as illustrated in FIG. 7. Initially, it will be understood that the evaluation of the pose may include various steps or procedures that are substantially identical to those discussed above, and, therefore, they will be discussed only briefly and the reference numerals will be augmented with the double prime. In this regard, the evaluation of an edge pose of the subject may occur in block 400" and evaluation of a pose of a tracked portion of the object may be made in block 404". The determined or recalled present gross geometry of the object may also occur in block 408" and a determination if any portion of the object contacts the subject portion may be made in block 412". As discussed above, if no deformation is determined in block 412", a NO path 420" may be followed to generate graphic representation in block 370. Again, the generation of the graphic may include a sub-process, such as generating a graphic representation of the object with no deformation in block 424" may occur. Following generation of the graphical representation in block 424", a display of the graphic representation may occur in block 374. However, as discussed above, if a determination of deformation occurring in block 412" does occur, a YES path 440" may be followed. The YES path 440 may be to a determination of whether the contacting portion is deformed in block 444". If it is determined that no deformation is occurring, a NO path 448" may be followed to generate a graphic representation of the object without deformation in block 424" and therefore, displaying the graphical representation in block 374.

Nevertheless, if deformation is determined to have occurred or is present, a YES path 460" may be followed to a learned geometry analysis which may be based upon a machine learning analysis or process in block 500. In the machine learning analysis in block 500, various learned or determined weights or categories may be used to analyze the determined portions in contact with the subject 412" and a determined present gross geometry of the object in block 408". For example, the pose of opposed subject portion edges may be determined to analyze or weight a stress or force applied to the object. The machine learning analysis may also evaluate or determine the number of movements or possible movements of portions of the implant 230.

As discussed above, and illustrated in FIG. 4D, the second portion 244 may include various portions that may also move relative to one another and/or the central axis 260. Accordingly, the machine learning analysis may include an evaluation or determination of movement of various portions relative to one another based upon the geometry evaluated in the image, such as the surface 220', as illustrated in FIG. 3A'. The analysis may include that the surface 220' is not flat or planar and may include various geometries other than in planar geometries to deform the implant 230 in a complex manner.

Further, the machine learning analysis may include loads and measures such as relating to force applied to the implant 230. For example, a determination of the gross geometry in block 408" may be used to analyze or evaluate a force applied to the implant 230 based upon the determined pose of the portions of the subject in block 404". A greater force applied to the implant 230 may include or cause a greater deformation that may be evaluated according to the machine learning analysis in block 500.

Regardless, the technique of the process in block 500 may be used to determine the optimal fit, as discussed above, to the determined edge portion of the subject portion. The optimal fit may, also therefore, be a fit to a selected threshold and/or include other considerations including those discussed above.

Accordingly, following the YES path 460 the geometry of the implant 230 may be evaluated according to the machine learning analysis in block 500. Following the machine learning analysis in block 500, a generation of a graphic representation of a deformed geometry of the implant may be made in block 470", similar to that discussed above. The graphical representation may then be displayed on the display device in block 374.

The determination of the graphical representation of the object, as discussed above, may also or alternatively be based in part or in total on the image representation and segmentation and a tracked pose of the object. As discussed above, the image data may be segmented. Thus, edges within the image may be identified. The tracked or determined pose of the object relative to the image portions may be used to determine a geometry of the object, such as a deformed geometry, within a region of interest such as due to contact with at least one of the edges in the image. Thus, the tracked pose or determined pose of the subject may not be required. Nevertheless, as discussed herein, the determined pose of the subject or subject portion in blocks 400, 400" may be used or be required to determine the configuration (e.g. deformed or not) of the object.

The machine learning analysis in block 500 may be used to evaluate and determine (e.g. segment) a geometry of subject image portions (e.g. vertebrae) to assist in determining a geometry of the implant 230 for display on the display device 32. Further, the geometry may also be analyzed or reviewed by the user 12. The user 12, or other appropriate user, may input to the navigation system 10 an actual or viewed geometry of the implant 230. Accordingly, the machine learning process 500 may be updated with the determined real geometry or evaluated geometry by the user to augment or change the machine learning algorithm. Thus, the machine learning analysis in block 500 may be updated or changed over time to achieve greater accuracy, if selected. It is understood that the machine learning analysis 500 may be any appropriate type of machine learning such as a neural network, forest or tree analysis, or categorization, or any appropriate analysis.

In various embodiments, machine learning could be utilized to continue to refine the physical/mechanical equations that would define how the implant would move relative to the segmented anatomical portions, such as the end plates on the vertebral body structures. Machine Learning could also be utilized to analyze surrounding tissue density to understand if there would be frictional interference that could change the expected geometry (or conversely, bodily fluids lowering friction in joints). Machine Learning could also be used to refine the modeling/geometry determining algorithms based on comparing the determined solution and an image taken of the actual configuration.

Regardless of the specific evaluation in block 364, as discussed above, the deformed geometry of the implant 230, due to a position between various portions of the subject, may be determined and displayed on the display device 32. Thus, the user 12 may have displayed on the display device a deformed geometry based upon contact of the implant 230 with the subject 20 and/or particular portions of the subject 20, such as the vertebrae 20*v*. The display device 32 may display the representation 280 of the implant 230 that more substantially matches (e.g. within a tolerable error) the geometry of the implant 230 and the subject due to the implant 230 contacting the subject 20. Further, as discussed above, the generation of the graphical representation 280 may occur substantially automatically by instructions being executed by the navigation system 10, including the processing unit 70 or any appropriate processing unit. Thus, the understanding of the geometry of the implant or display of the geometry of the implant in the graphical representation 280 may be substantially immediate or in real time and not require additional input or altering by the user 12. Thus the deformed or altered graphical representation 280 may be understood to be substantially automatic.

The system, such as the navigation system 10, as discussed above, may be used to determine and illustrate the present pose and configuration of an object, such as the implant 230, relative to portions of the subject 20. The determination of the configuration, including the pose and geometric outline of the object may be based upon the evaluated pose and surfaces of the subject 20 and the tracked and navigated pose thereof. Similarly, or in addition thereto, a determination/or plan may be made by evaluating information of the subject 20 and/or a selection or data base of possible treatment objects.

As discussed above, and illustrated in FIG. 8, various portions of an anatomy, such as the vertebrae 20*vi* and a second vertebrae 20*vii* may be included in image data. The analyzed image data, as discussed herein, may be used to assist in determining or planning a procedure. For example, selecting an appropriate implant or designing an appropriate implant.

The image data may be acquired in any appropriate manner, such as that discussed above. Further, the image data may include various information such as included in a three-dimensional model, two-dimensional planar images, or a plurality of two-dimensional images or projections. The image data may also include a plurality of types of data that are acquired and melded together, such as a computer tomography (CT) or a magnetic resonance image (MRI) that may include three-dimensional image data and a planar x-ray image that includes a projection through the subject 20. Regardless, the vertebrae may be included in image data 550 that may be analyzed and/or displayed with the display device 32.

In various embodiments, the image 550 need not be displayed in a pre-analysis or raw configuration, but may be displayed with the display device 32 after a selected analysis of the image 550. Analysis of the image may include various process steps, such as segmenting various portions of the data 550 including the respective vertebrae 20*vi*, 20*vii*. The segmentation may include identification of one or more boundaries or edges of the vertebrae including the boundaries, as discussed above, including the respective superior vertebral body boundaries 210, 220 and inferior vertebral body boundaries 214, 224. It is understood that additional boundaries or edges may also be identified, such as spinous process boundaries, facets, and the like. Further, it is understood that that boundaries 210-224 may be two-dimensional or three-dimensional boundaries. Accordingly, as illustrated in FIG. 8, the boundaries 210-224 may be analyzed, when it is determined.

With continuing reference to FIG. 8 and additional reference to FIG. 9, the surface geometry or shape of the respective vertebrae 20*vi*, 20*vii* may also be delineated and/or analyzed. For example, the surface 214 may include an irregular geometry, including a substantially non-planar surface. For example, a first outer portion 214*a* may be at a distance below a plane defined by a second portion 214*b*. Accordingly, the surface 214 may be substantially non-planar and include a three-dimensional configuration that may be analyzed and delineated according to selected techniques. As discussed above, a segmentation algorithm, machine learning (e.g. convolutional neural network) systems, or the like may be used to determine the geometry of identified portions in the image 550. It is further understood that the segmentation of the image 550 may be based upon input by the user 12, such as the user 12 identifying one or more points (e.g. pixels or voxels) in the image 550 as a seed to assist in segmentation and/or delineation thereof. Further, the user may identify various portions or surfaces to be delineated for further analysis, such as the inferior and superior plates of the bodies of the vertebrae 20*v* in the image 20*vi*, 20*vii*. Further the second vertebrae 20*vii* may include the surface 220 that may also have geometry, or may be substantially planar, as illustrated in FIG. 9.

Accordingly with continuing reference to FIG. 8 and FIG. 9, a relative geometry and/or space may be generated and/or determined between the two vertebrae 20*vi*, 20*vii*. For example, a geometry including one or more distances between portions of the vertebrae 20*vi*, 20*vii* may be determined. For example, a first distance may be determined between a mid-lateral point 560 of the first vertebrae 20vi and a mid-lateral first lateral point 562 of the second vertebrae 20vii. Similarly a second distance 568 may be measured between a third mid-lateral point 572 and a fourth mid-lateral point 576. The distances 558, 568 may differ due to the surface geometry and configuration of the respective surfaces 214, 220. For example, as discussed above, the second portion 214b may extend further from the opposing surface 210 and the first portion 214a and, therefore, the distance 568 extending therefrom, may be less than the distance 558.

It is understood that a plurality of distances may be measured between the two opposing surfaces 214, 220 of the respective vertebrae 20vi, 20vii. In various embodiments the plurality of distances may be used to generally define a three-dimensional shape between the two vertebrae 20vi, 20vii. The area or volume between the two vertebrae 20vi, 20vii, may be a region of interest (ROI) geometry. The ROI geometry may be determined or define in any appropriate manner and, in various embodiments, include a selected geometric shape, such as cylinder, may be morphed or interpolated, using appropriate techniques, until it substantially matches the distance or configuration between the two vertebrae 20vi, 20vii. For example, as illustrated in FIG. 8, a cylinder 590 may be positioned between the two vertebrae surfaces 214, 220 and augmented or changed until a geometry between the two vertebrae 20vi, 20vii substantially matched by the virtual cylinder 590. The geometry of the virtual cylinder 590, therefore, may be used to match the surfaces 214, 220 and/or the distances or geometric configuration (e.g. three dimensional configuration) between the surfaces 214, 220. Thus, the geometry between the two surfaces 214, 220 may be understood or analyzed according to the appropriate techniques to determine a geometry and/or volume between the two surfaces 214, 220.

As discussed above, the area or volume between selected portions, such as the surface 214 and the surface 220 may be identified including the morphology (e.g. geometry of a structure, such as complex structure), between the two surfaces. The volume of morphology may be bounded by a selected bounding or surface, such as a cylinder that has a diameter that would fit within an external boundary of the surface 214 such as a diameter 600. It is understood that the diameter 600 may be any appropriate external boundary shape or geometry and a diameter or circle is merely exemplary. Nevertheless, a cylinder 590 may be defined by the size, length, and geometry in the circle or boundary 600. It is understood that the cylinder 590 may not be a perfect cylinder, and may be a complex shape including an angle or bent area or region 604. The morphology of the area, such as the cylinder 590, may be used to define the geometry of a volume between the two surfaces 214, 220. As discussed above, the identification of the surfaces 214, 220 are due to the selected segmentation of the image may be used to identify a region or volume between the two surfaces 214, 220. This definition, such as the geometric definition of the cylinder 590, may be used for various purposes, such as those discussed herein.

Accordingly, with reference to FIGS. 8 and 9 and additional reference to FIG. 10, the determined cylinder or interspace volume 590 and various geometry thereof, such as the boundary 600, may be used to assist in select or plan a prosthesis, such as the prosthesis, as discussed above or herein, to be positioned within the volume 590 determined between the two vertebrae 20vi, 20vii. The determined geometry of a volume may be compared, as schematically illustrated in FIG. 10, to one or more possible implants. The comparison may occur through a visual comparison, such as a display on the display device 32, a graphical or automatic comparison, or any other appropriate comparison.

For example, a plurality of implants or implant configuration may include a first implant 620, a second implant 624, and a third implant 628. Each of the implants 620, 624, 628 may have respective models, such as CAD models, that may include information such as dimensions, geometries, and possible changes in geometry. As illustrated above, the implant 230 may include two portions such as the first portion 240 and a second portion 244. As discussed above, the new portions may move relative to one another due to the movement or adjustment member 246. The portions may also then rotate, such as the second portion 244 may rotate relative to a long axis 260 of the implant 230. Therefore, CAD models of the various implants 620, 628 may include similar information.

Briefly, the first implant 620 may have at least one known and fixed length 632. A second or adjustable end may rotate or be adjustable to have a selected angle, such as a range between a first contacting surface configuration 638, having a first angle 640 relative to a long axis 644 of the implant, and the second configuration surface 650, having a second angle 654 relative to the long axis 644. Further, dimensions of the respective surfaces 638, 650 relative to a first end 658 of the first portion or a fixed portions 660 may be determined. Thus, the first implant 620 may be defined by the possible positions of the end surface 638, 650 relative to the first end 658 and dimensions relative thereto.

The second implant 624 may also include a first surface 680 of a first portion 684 that has a first length 688. Similarly the end surface may have a first configuration 692 or 694 in an implant configuration that may be at respective different angles 696, 698, relative to a long axis 704 of the implant 624. Again, the various dimensions and/or possible position geometries may be included in the CAD model. Finally, for example, the implant 628 may include a plurality of portions such as a first portion 710 and a second portion 714. The first portion 710 may be substantially fixed or rigid, such as in a substantially cylindrical or rectangular shape or configuration. A second portion 714 may be similar to the first implant 620, 624 and include a configurable or changeable terminal end surface 720. Accordingly, the second portion 714 may be adjusted, such as discussed above, and will not be repeated here understood by one skilled in the art. Further, one skilled in the art will understand that the portions 710, 714 of the third implant 628 may be connected together to form an implant and/or implanted separately to what is implanted.

Regardless, the geometry, including the cylinder 690 and/or any determined geometry (e.g. the outer geometry 600) may be compared to the various possible configurations of the implant 620, 624, 628 to attempt to find the optimal fit, as discussed above. In various embodiments, the optimal fit may be determined relative to a threshold. For example, that the selected or possible implant may fill a selected amount (e.g. at least 90%) of the determined volume but not be greater than the determined volume. In various embodiments, regardless of the selected one or more criteria, selected algorithms may be determined or refined based on the mechanical and physical dynamics allowed by the implant.

For example, the process or system, such as the navigation processor 66 and/or the image processing unit 76, or other appropriate processing unit (e.g. a planning processor system that may be incorporated into a separate workstation or computer). The one or more processors may execute instructions to compare the possible geometries of various implants, such as the implant 620, to the geometry of the cylinder 590. Various comparative techniques may be used, such as at least squares fit to attempt to fill the volume 590 with possible configurations of the implant 620. It is understood that a plurality of attempts may be made, such as trying each of the three implants 620, 624, 628 or a planning strategy may be determined based upon a selected fit criteria. It is further understood that more or less than the three end plates illustrated in FIG. 10 may be attempted and/or planned with and these three are merely exemplary.

Continuing reference to FIGS. 8-10, and additional reference to FIG. 11, a planning flow chart or process 750 is illustrated. The flow chart 750 may be a process that can be executed by a selected processor, such as those discussed above. The instructions may be stored in a selected memory, also including those discussed above, to be accessed by the processor. Accordingly, the process 750 may be understood to be computer executable instructions.

Accordingly the process 750 may begin at start block 754. The process may then access subject data in block 756 and the image data may be segmented or delineated in block 760. The accessed subject image data and segmentation of subject image data may include processes a discussed above, and will not be repeated here in detail. Nevertheless, after the image data is segmented in block 760 a determination or selection of a subject implant region or a region of interest (ROI) may be made in block 764.

The selection of a subject implant region or region of interest may include a region between two vertebrae, such as the vertebrae 20vi, 20vii. In various embodiments, for example as discussed above, the user 12 may view the image and identify a region of interest between the two surfaces 214, 220. It is understood, however, that the user may also identify other regions, however, the process 750 may be used to analyze a region between two vertebrae or two surfaces 214, 220, as discussed above. The determination may be made by the user such as by selecting the surfaces 214, 220 that have been segmented in the image data, user identifying or selecting a plurality of points in the image, or other appropriate mechanisms. This allows a determination or a selection of an implant region or ROI may be selected in block 764.

An analysis of the ROI is made in block 768. The analysis may include further segmentation, such as selecting two regions of a surface, such as the surface 214 including the first region 214a and the second regions 214b. The analysis may include determining whether certain surfaces include a variation great enough to require a further segmentation or separation, or other appropriate analysis.

After analyzing the ROI in block 768, a determination of a volume geometry of the implant region or ROI is made in block 772. A determination of the volume geometry may include portions or steps, as discussed above, including the determination of the outline or boundary 600, the cylinder 590, and various other geometries, such as the offset region 604. The determination of the region geometry may be made in block 772, as discussed above. The geometry may be saved in block 776, if selected, and therefore is understood not to be required.

With the determined geometry in block 772, a recall or input of one or more object model geometries may be made in block 780. The model geometry may include the various geometries and/or note the change or configurable geometries as discussed above. For example, as illustrated in FIG. 10, various implants, including more than one implant, may include a variable geometry that may be selected by a user during implantation and/or use. The object model may include this information for analysis or selection, as discussed further herein. Accordingly, the object model geometry may include various geometry and/or variability for comparison to the volume geometry. The recalled model may include a geometry that is known or determined. The geometry, or possible geometries in light of the plurality of configurations due to one or more configurable portions, may be included in the model.

A comparison of the volume geometry to one object model geometry may be made in block 784. The comparison may include determining whether the model may be fit within the selected volume, such as the cylinder volume 590, as discussed above. The comparison may include determining all possible geometries of the one object model geometry implant that is compered in block 784. Thus, the comparison may include an analysis of the model and the geometry or geometries able to be achieved by the object.

As discussed above various comparison or fit methods may be made or used to determine a best fit (as is understood by one skilled in the art), such as a least squared fit, which may be used to determine whether the model will fit within the volume geometry to a selected degree. Various thresholds may be determined for a proper or selected fit, as is understood by one skilled in the art. Thus, the analysis of the model may be used to determine whether the related object may be used to fit or fill the ROI geometry, such as the cylinder 590, to the selected threshold.

After the comparison in block 784, a determination of whether the object model geometry fits the volume geometry may be made in block 790. The determination may follow a NO path, if the geometry does not fit to a selected threshold or degree to return to compare the volume geometry to an object model geometry in block 784. It is understood that the comparison in the loop or iteration 794 may be within a separate or different model geometry. Further, the loop may also include a change to the model geometry, such as an adjustment of an angle of an end, as the various models may include abilities to change geometry due to adjustments by the user. Accordingly, the iterative loop 794 may allow for comparison of a plurality of geometries of different implants and/or a plurality of geometry of a single implant. Nevertheless, more than one comparison may occur in the iterative loop 794 until the determination 790 reaches a selected number of comparison steps (e.g. termination after 15, 20, 25, or a selected number of comparisons) or when a model matches or fits the volume geometry selected degree. Thereafter a YES path 798 may be followed.

With following the YES path 798, an output of an identification of the object model geometry that fits the volume geometry may be made in block 802. The output may include a visual or physical output, such as an illustration on the display device 32 of a selected implant. The output may include a selected size, name, identification number, or other appropriate identification information to allow for a selection or retrieval of an appropriate implant.

For example, the process 750 may be performed after acquiring image data of the subject 20 during a planning phase. Thus, during a planning phase the identification of the object model for a selected object or implant may be made such that the implant may be obtained and provided for a selected procedure. The output, therefore, may also include a transmission of a purchase order, or other information to a provider to supply an implant. Further, the output may include output of selected geometric configurations, such as a length, or the like that the selected implant will be positioned at during a procedure. Accordingly, the output may include identification of a selected implant in block 802.

The process 750 may then end or terminate at end block 810. It is understood that the end block 810 need not be the final termination of the procedure, but may be the end after determining or outputting identification of an object model or object for a selected procedure. Accordingly, any of these steps may occur in the end block and/or after the end block such as obtaining prosthesis, implanting a prosthesis, or other appropriate steps.

Nevertheless, as discussed above, the data of a subject, such as image data, may be analyzed for various purposes. The image data may be analyzed to allow for a determination of a possible or real time geometry of an implant due to a known or navigated position or a pose of an implant relative to navigated or known poses of portions of a subject, such as a vertebrae. Thus the implant may be illustrated on the display device 32 in a real time pose and configuration for understanding by the user 12. Further, the analyzed geometry may be used to select or propose an implant for a selected procedure, as discussed above.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium (e.g. memory module) and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors (e.g. processor module), such as one or more digital signal processors (DSPs), general purpose microprocessors, graphic processing units (GPUs), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of automatically determining a geometry of an implant, comprising:
   accessing image data of a subject having identified at least a first portion and a second portion of the subject;
   determining a pose of the implant relative to a pose of the first portion of the subject and a pose of the second portion of the subject, wherein the implant includes at least a first portion independently moveable relative to a second implant portion;
   determining a geometry of a region of interest between the first portion of the subject and the second portion of the subject with a processor;
   determining a geometry of the implant including the first implant portion and the second implant portion in the determined pose of the implant based at least on the determined geometry of the region of interest and wherein the geometry of the implant includes at least a shape that is operable to fit within an external boundary defined and determined by the determined geometry of the region of interest with the processor; and
   displaying the determined geometry of the implant for assisting in performing a procedure.

2. The method of claim 1, wherein determining a geometry of the implant in the determined pose of the implant includes constraining the determined geometry of the implant by the geometry of the region of interest.

3. The method of claim 1, further comprising:
   tracking the first portion of the subject;
   tracking the second portion of the subject;
   tracking the implant;
   wherein determining the pose of the implant relative to the pose of the first portion of the subject and the pose of the second portion of the subject is determined via the tracking of the implant, the tracking of the first portion of the subject, and the tracking of the second portion of the subject;
   wherein the first implant portion is configured to be coupled to and interact with the second implant portion.

4. The method of claim 1, further comprising:
   determining at least a first edge of the first portion of the subject and a second edge of the second portion of the subject;
   wherein the determined first edge of the first portion and the second edge of the second portion is operable to determine a geometry relative to the determined first edge of the first portion and the second edge of the second portion.

5. The method of claim 4, wherein determining at least the first edge of the first portion of the subject and the second edge of the second portion of the subject includes automatically segmenting the first edge and the second edge;

wherein the identified first portion of the subject and the second portion of the subject are segmented.

6. The method of claim 4, further comprising:
accessing a model of the implant, wherein the model includes at least (i) a dimension of a rigid portion of the implant and (ii) possible configurations of a moveable portion of the implant; and
determining whether the implant is in contact with at least the first edge or the second edge;
wherein determining the geometry of the implant in the determined pose of the implant includes evaluating the accessed model based on the determination of whether the implant is in contact with at least the first edge.

7. The method of claim 6, wherein evaluating the accessed model based on the determination of whether the implant is in contact with at least the first edge or the second edge, comprises:
evaluating an edge geometry of at least the first edge or the second edge;
evaluating the possible configurations of the moveable portion of the implant;
determining an optimal fit of the possible configurations of the moveable portion of the implant when in contact with the evaluated edge geometry of at least the first edge or the second edge.

8. The method of claim 7, wherein evaluating the edge geometry of at least the first edge or the second edge includes evaluating a geometry of an end plate of a vertebral body.

9. The method of claim 7, wherein determining the optimal fit of the possible configurations of the moveable portion of the implant when in contact with the evaluated edge geometry of at least the first edge or the second edge comprises evaluating algorithms related to the implant regarding the possible configurations based on the determination of whether the implant is in contact with at least the first edge or the second edge and the evaluated edge geometry of at least the first edge or the second edge.

10. The method of claim 6, wherein displaying the determined geometry of the implant includes generating a graphical representation of the implant based on at least the determined geometry of the implant in the determined pose of the object including evaluating the accessed model based on the determination of whether the implant is in contact with at least the first edge or the second edge.

11. The method of claim 10, wherein displaying the determined geometry of the implant further comprises:
displaying the generated graphical representation; and
updating the displayed graphical representation in real time based at least on the tracking the first portion of the subject, tracking the second portion of the subject, and tracking the implant.

12. The method of claim 6, wherein accessing the model includes executing instructions with a processor to recall from a memory the model.

13. A method of determining a geometry of an implant for a surgical procedure, the method comprising:
accessing image data of a subject having identified at least a first portion of the subject and a second portion of the subject;
determining a pose of the first portion of the subject based on tracking the first portion;
determining a pose of the second portion of the subject based on tracking the second portion;
determining a geometry of a region of interest between the first portion of the subject and second portion of the subject with a processor based on the determined pose of the first portion of the subject and the determined pose of the second portion of the subject;
determining a pose of the implant relative to the first portion of the subject and the second portion of the subject, wherein the implant includes a configurable portion operable to be independently moved relative to a rigid portion;
determining whether the implant has at least a configurable portion contacting at the first portion of the subject based on the determined pose of the implant;
determining a geometry of the implant in the determined pose of the implant based at least on the determination of whether the configurable portion is contacting at least one of the first portion or the second portion, wherein the geometry of the implant in the determined pose of the implant includes at least a shape that is operable to fit within an external boundary determined and defined by the determined geometry of the region of interest with the processor.

14. The method of claim 13, further comprising:
tracking the first portion of the subject, wherein determining the pose of the first portion of the subject is based on tracking the first portion;
tracking the second portion of the subject, wherein determining the pose of the second portion of the subject based on tracking the second portion; and
tracking the implant, wherein determining a pose of the implant relative to the first portion of the subject and the second portion of the subject.

15. The method of claim 14, further comprising:
evaluating the accessed image data to determine at least a first edge of the first portion and a second edge of the second portion; and
determining a geometry of at least one of the first edge or the second edge;
wherein the implant is configured to contact at least the first edge.

16. The method of claim 15, further comprising:
accessing a model of the implant, wherein the model includes at least (i) a dimension of the rigid portion of the implant and (ii) a plurality of possible configurations of the configurable portion of the implant; and
wherein determining the geometry of the implant in the determined third pose includes evaluating the accessed model based on the determination of whether the configurable portion of the implant (i) is in contact with at least the first edge or the second edge and (ii) the determined geometry of at least the first edge or the second edge.

17. The method of claim 16, wherein determining the geometry of the implant in the determined third pose further includes determining a fit of at least one configuration of the plurality of possible configurations of the configurable portion of the implant when in contact with at least the first edge or the second edge;
wherein tracking the implant includes tracking the rigid portion.

18. The method of claim 13, further comprising:
generating a graphical representation of the implant based on the determined geometry;
wherein the implant is contacting the first portion and the second portion.

* * * * *

UNITED STATES PATENT AND TRADEMARK OFFICE
CERTIFICATE OF CORRECTION

PATENT NO. : 11,890,060 B2
APPLICATION NO. : 16/861356
DATED : February 6, 2024
INVENTOR(S) : Matthew W. Koenig et al.

It is certified that error appears in the above-identified patent and that said Letters Patent is hereby corrected as shown below:

In the Specification

Column 4, Detailed Description, Line 55, Delete "30" and insert --32-- therefor

Column 5, Detailed Description, Line 43, Delete "40," and insert --42,-- therefor Column 6, Detailed Description, Line 5, Delete "72" and insert --74-- therefor Column 6, Detailed Description, Line 12, Delete "66." and insert --70.-- therefor Column 10, Detailed Description, Line 67, Delete "240" and insert --244-- therefor Column 11, Detailed Description, Line 9, Delete "234" and insert --230-- therefor Column 12, Detailed Description, Line 24, Delete "positons" and insert --positions-- therefor Column 14, Detailed Description, Line 1, Delete "230." and insert --234.-- therefor Column 15, Detailed Description, Line 31, Delete "300," and insert --320,-- therefor Column 22, Detailed Description, Line 50, Delete "690" and insert --590-- therefor Signed and Sealed this
Twelfth Day of November, 2024

Katherine Kelly Vidal
*Director of the United States Patent and Trademark Office*